United States Patent
Gusarova et al.

(10) Patent No.: US 11,977,081 B2
(45) Date of Patent: May 7, 2024

(54) ANGPTL8 ASSAY AND USES THEREOF

(71) Applicant: REGENERON PHARMACEUTICALS, INC., Tarrytown, NY (US)

(72) Inventors: Viktoria Gusarova, Pleasantville, NY (US); Jesper Gromada, Scarsdale, NY (US); Andrew J. Murphy, Croton-on-Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 790 days.

(21) Appl. No.: 16/954,918

(22) PCT Filed: Dec. 18, 2018

(86) PCT No.: PCT/US2018/066266
§ 371 (c)(1),
(2) Date: Jun. 17, 2020

(87) PCT Pub. No.: WO2019/126194
PCT Pub. Date: Jun. 27, 2019

(65) Prior Publication Data
US 2020/0393470 A1   Dec. 17, 2020

Related U.S. Application Data

(60) Provisional application No. 62/599,911, filed on Dec. 18, 2017.

(51) Int. Cl.
*G01N 33/53* (2006.01)
*G01N 33/68* (2006.01)

(52) U.S. Cl.
CPC ... *G01N 33/6857* (2013.01); *G01N 2800/044* (2013.01)

(58) Field of Classification Search
None
See application file for complete search history.

(56) References Cited

U.S. PATENT DOCUMENTS

| | | | |
|---|---|---|---|
| 6,569,992 B1 | 5/2003 | LaFleur | |
| 7,157,247 B2 | 1/2007 | Botstein | |
| 7,244,816 B2 | 7/2007 | Botstein | |
| 7,368,531 B2 | 5/2008 | Rosen | |
| 7,393,663 B2 | 7/2008 | Edwards | |
| 10,259,870 B2 | 4/2019 | Gusarova et al. | |
| 10,442,856 B2 | 10/2019 | Gusarova | |
| 10,774,139 B2 * | 9/2020 | Chu | A61P 3/06 |
| 2003/0211096 A1 | 11/2003 | Ashkenazi | |
| 2012/0128679 A1 | 5/2012 | Okamoto | |
| 2017/0037124 A1 | 2/2017 | Gusarova et al. | |
| 2017/0291937 A1 | 10/2017 | Gromada | |
| 2018/0134781 A1 | 5/2018 | Gusarova | |
| 2020/0377583 A1 | 12/2020 | Gromada | |
| 2022/0127348 A1 | 4/2022 | Gromada | |

FOREIGN PATENT DOCUMENTS

| | | |
|---|---|---|
| WO | 2012/148873 | 11/2012 |
| WO | 2012/174178 | 12/2012 |
| WO | 2016/054494 | 4/2016 |
| WO | 2017027316 | 2/2017 |
| WO | 2017177181 | 12/2017 |

OTHER PUBLICATIONS

Jordan, William; Antigen Measurement Using ELISA, The Protein Protocols Handbook, 2nd edition, 2002, pp. 1083-1088. (Year: 2002).*
Arias-Loste et al., Plasma betatrophin levels in patients with liver cirrhosis, World Journal of Gastroenterology, Oct. 7, 2015, vol. 21, Issue 37, pp. 10662-10668. (Year: 2015).*
Voller Alister, The Enzyme Linked Immunosorbent Assay Diagnostic Horizons, Dynasciences Corportion, Published by Microbiological Associates, vol. 2, No. 1, Feb. 1978, pp. 1-7. (Year: 1978).*
Arigobo Biolaboratories, "Product Data Sheet—Purified anti-Betatrophin (ANGPTL8)", (Jul. 25, 2014), BioLegend, URL: http://www.biolegend.com/pop_pdf?id=10113, (Nov. 8, 2016), XP002763965, 3 pages.
Calandra et al., "Familial combined hypolipidemia due to mutations in the ANGPTL3 gene", Clinical Lipidology, 2013, 8: 1, 81-95.
Chen, Jiaxi et al., "In vivo targeted delivery of ANGPTL8 gene for beta cell regeneration in rats", Feb. 28, 2015, Diabetologia 58(5):136-1044.
Fenzl et al., "Circulating betatrophin correlates with atherogenic lipid profiles but not with glucose and insulin levels in insulin-resistant individuals", Diabetologia (2014), 57(6), 1204-1208.
Fu, Zhiyao et al., "A Lipasin/ANGPTL8 Monoclonal Antibody Lowers Mouse Serum Triglycerides Involving Increased Postprandial Activity of the Cardiac Lipoprotein C6 Lipase", (Dec. 21, 2015) Scientific Reports 5(1):5.
Gusarova, Viktoria, et al., "ANGPTL8 Blockage with a Monoclonal Antibody Promotes Triglyceride Clearance, Energy Expenditure, and Weight Loss in Mice," Endocrinology, vol. 158, No. 5, May 1, 2017, pp. 1252-1259, XP055443231.
Haller, Jorge F., et al., "ANGPTL8 requires ANGPTL3 to inhibit lipoprotein lipase and plasma triglyceride clearance," Journal of Lipid Research, vol. 58, No. 6, Jun. 1, 2017, pp. 1166-1173, XP55387875.

(Continued)

*Primary Examiner* — Gary Counts
(74) *Attorney, Agent, or Firm* — MERCHANT & GOULD P.C.

(57) ABSTRACT

The present invention provides ELISA-based methods for detecting and/or quantifying ANGPTL8 in biological samples using anti-ANGPTL8 antibodies.

13 Claims, 11 Drawing Sheets
Specification includes a Sequence Listing.

(56) References Cited

OTHER PUBLICATIONS

Hanson, Robert L. et al., "The ARG59Trp Variant in ANGPTL8 (betatrophin) is Associated with Total and HDL-Cholesterol in American Indians and Mexican Americans and Differentially Affects Cleavage of ANGPTL3", Molecular Genetics and Metabolism Academic Press, Amsterdam, NL, 118(2):128-137, 2016.

Nohara et al., "Impact of Betatrophin (ANGPTL8) R59W Mutation for Future Diabetes, and Minimal Modification of Circulating Betatrophin With Strong Statins", Circulation, (Nov. 10, 2015), vol. 132, Supp. Suppl. 3. Abstract No. 18157, 1 page.

Zhang, Ren, "The ANGPTL3-4-8 model, a molecular mechanism for triglyceride trafficking," Open Biology, vol. 6, No. 4, Apr. 1, 2016, pp. 150727, XP55387866.

Product Data Sheet, "Purified anti-Betatrophin (ANGPTL8)", BioLegend, XP-002763965, Revision Date Jul. 25, 2014, 1 page.

Zhang et al., "A Monoclonal Neutralizing Antibody Against Lipasin (Angptl8), a Novel Lipid Regulator, Reduces Serum Triglycerides in Mice By Enhancing Lipoprotein Lipase-Mediated Triglyceride Clearance", Endocrine Society's 97th Annual Meeting and Expo, Mar. 5-8, 2015, San Diego, CA. Abstract# OR13-6, 1 page.

Zhang et al., "Emerging Roles of Lipasin as a Critical Lipid Regulator", (2013) Biochemical and Biophysical Research Communications 432:401-405.

Zhang, "Lipasin, a novel nutritionally-regulated liver-enriched factor that regulates serum triglyceride levels", (2012) Biochem Biophys Res Commun, http://dx.doi.org/10.1016/j.bbrc.2012.07.038.

Quagliarini, Fabina et al., "Atypical angiopoietin-like protein that regulates ANGPTL3", Proc Natl Acad Sci USA, Nov. 27, 2012, pp. 19751-19756.

Wang, Yan, et al., "Mice lacking ANGPTL8 (Betatrophin) manifest disrupted triglyceride metabolism without impaired glucose homeostasis", PNAS, Oct. 1, 2013, vol. 10, No. 40, pp. 16109-16114.

\* cited by examiner

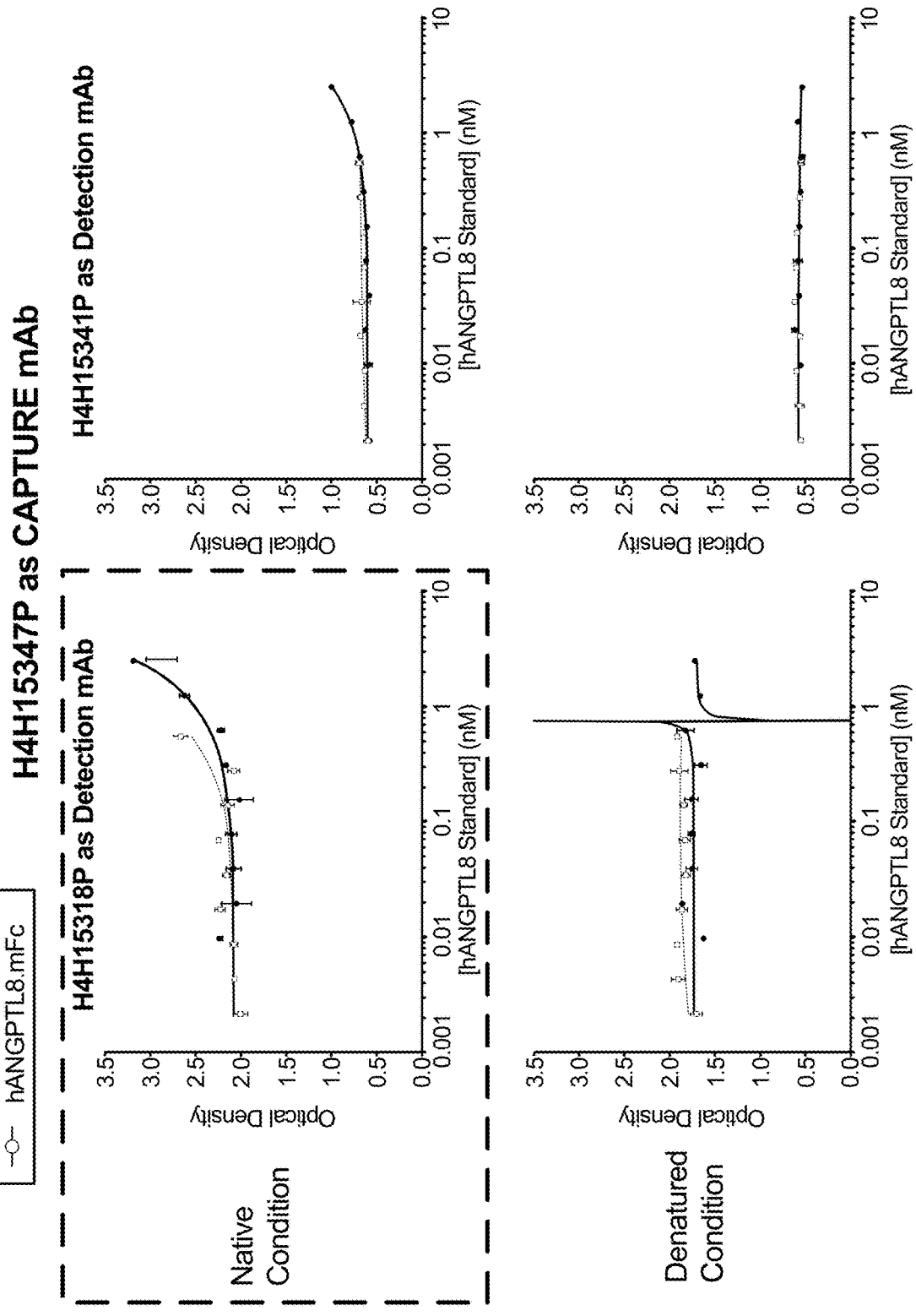

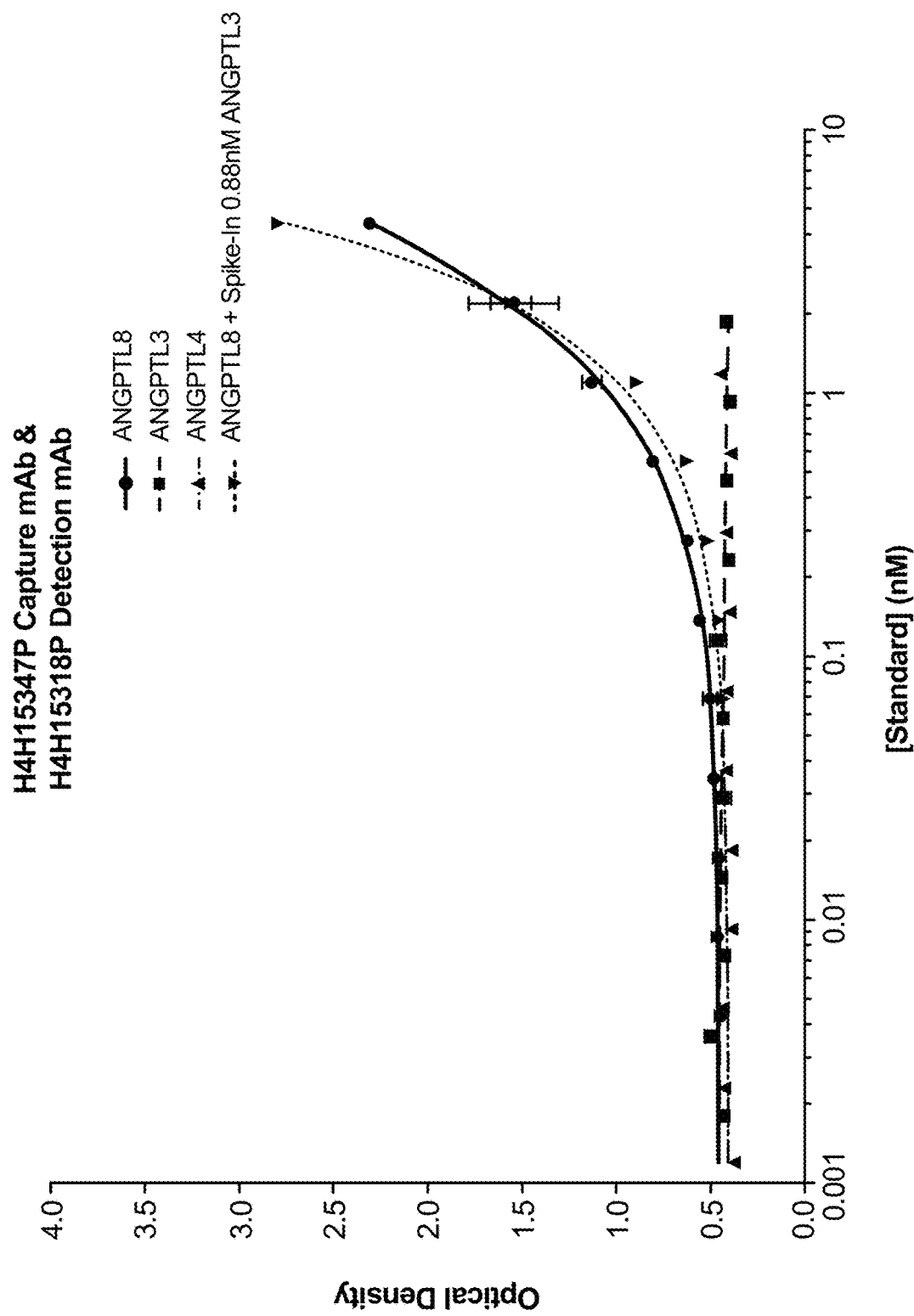

ANGPTL8 ASSAY AND USES THEREOF

This application a U.S. National Stage application of PCT/US2018/066266, filed on Dec. 18, 2018, which claims the benefit of priority to U.S. provisional application No. 62/599,911, filed on Dec. 18, 2017, which applications are incorporated herein by reference. To the extent appropriate, a claim of priority is made to each of the above-disclosed applications.

SEQUENCE STATEMENT

The instant application contains a Sequence Listing, which has been submitted electronically in ASCII format and is hereby incorporated by reference in its entirety. Said ASCII copy, created on Dec. 18, 2017 and updated on Jun. 17, 2020, is named Sequence_Listing.txt and is 154,505 bytes (150 KB) in size.

FIELD OF THE INVENTION

The present invention relates to diagnostic tests and assay methods for detecting angiopoietin-like protein (ANGPTL) 8 levels in a subject and for identifying capture and detection monoclonal antibodies and/or fragments thereof that specifically bind ANGPTL8.

BACKGROUND

ANGPTL8 (alternatively called TD26, RIFL, Lipasin, C19orf80 and Betatrophin) is an ANGPTL family member that has been implicated in both triglyceride (TG) and glucose metabolism. It is a circulating protein that is expressed primarily in liver and adipose tissue. Unlike ANGPTL3 and ANGPTL4, ANGPTL8 lacks a fibrinogen-like domain at the C-terminus, but contains an N-terminal coiled-coil domain, much like other ANGPTL family members. Phylogenetic analysis reveals that ANGPTL8 shares common ancestors with ANGPTL3 and ANGPTL4 (Fu, Z. et. al., (2013), Biochem. Biophys. Res. Commun. 430:1126-1131).

Hepatic overexpression of ANGPTL8 is associated with hypertriglyceridemia, whereas inactivation of Angptl8 causes a reduction in plasma TG levels (Quagliarini, F. et. al. (2012), Proc. Natl. Acad. Sci. USA 109(48):19751-19756; Wang, Y. et. al. (2013), Proc. Natl. Acad. Sci. USA 110: 16109-16114). Despite the consensus that ANGPTL8 is involved in lipid regulation, the mechanism responsible for this process is still under debate. One proposed mechanism is that ANGPTL8 inhibits lipoprotein lipase (LPL) activity, resulting in reduced triglyceride hydrolysis and clearance (Zhang, R. et. al., (2012), Biochem. Biophys. Res. Commun. 424:786-792).

ANGPTL8 has also been reported to play a role in beta cell proliferation and beta cell mass in mice, where insulin resistance was induced by an insulin receptor antagonist, S961 (Yi, P. et. al. (2013), Cell 153:747-758). However, subsequent studies revealed that ANGPTL8 is not required for beta cell function, or the beta cell growth response to insulin resistance. Furthermore, overexpression of ANGPTL8 does not increase beta cell area or improve glycemic control (Gusarova, V. et. al. (2014) Cell 159:691-696). Hepatic overexpression of ANGPTL8 is associated with hypertriglyceridemia.

Given the role of ANGPTL8 in hypertriglyceridemia and other disorders or conditions associated with elevated triglyceride and lipid levels, it could be beneficial to be able to assess the presence and/or level of ANGPTL8 in a subject in order to determine a need for treatment or to monitor the amount of ANGPTL8 during treatment and/or at the time of completion of treatment. Such a test or assay method would provide information as to whether a patient needs or is responding to treatment, and, as such, it may also allow for a determination as to whether the patient will be adequately protected by the therapy. Such a test or assay method would also aid in the determination of when a patient can initiate or terminate maintenance therapy. An unmet need exists in the art for the development of such a diagnostic test that is specific to and effective for ANGPTL8 and ANGPTL8-associated disorders, or an assay method for determining the safety, efficacy, or outcome of therapy.

Such a test or assay method would provide information as to the level of ANGPTL8 in a subject and could also provide information as to the strength and specificity of binding of an ANGPTL8 antagonist.

BRIEF SUMMARY OF THE INVENTION

There is a need for a commercial ELISA for the evaluation of ANGPTL8 levels in humans. ANGPTL8 levels correlate with many diseases, including, without limitation, obesity, Type 2 diabetes, metabolic syndrome, non-alcoholic steatohepatitis (NASH), and the like. However, most known ELISAs do not yield accurate or reproducible results for ANGPTL8 measurement. Disclosed herein is a method for evaluating ANGPTL8 level(s) in different disease populations, including in previously sequenced cohorts, and for conducting an analysis of humans from these populations to determine whether or not ANGPTL8 level(s) indeed correlate(s) with specific diseases, as well as to evaluate whether or not ANGPTL8 is a or the factor causing the disease and/or can be used as a circulating biomarker to predict the development or presence of the disease.

In one aspect, the invention provides a method for detecting and/or quantifying human Angiopoietin-like protein 8 (hANGPTL8) in a sample, the method comprising:
  Obtaining a sample from a subject;
  Adding the sample to the wells of an Enzyme Linked Immunosorbent Assay (ELISA) plate coated with a capture antibody, wherein the capture antibody is a first anti-hANGPTL8 antibody;
  Adding a detection antibody to the wells of the plate, wherein the detection antibody is a second anti-hANGPTL8 antibody bound to a tag;
  Adding an agent that binds the tag, wherein the agent is conjugated to an enzyme;
  Adding a substrate for the enzyme; and
  Measuring the amount of product of the enzyme-substrate reaction.

In one embodiment, the measuring comprises reading the absorbance with a spectrophotometer.

In one embodiment, the agent is avidin or streptavidin. In another embodiment, the enzyme is horseradish peroxidase (HRP) or alkaline phosphatase. In still another embodiment, the enzyme is HRP.

In one embodiment, the tag is selected from the group consisting of a fluorescence label, a radiolabel, an enzyme label, a luminescent label, an electrochemical, or a visual label. In another embodiment, the tag is biotin.

In one embodiment, the inventive method detects and/or quantifies human Angiopoietin-like protein 8 (hANGPTL8) in a sample, but does not detect (and/or quantify) non-human ANGPTL8. In another embodiment, the inventive method detects and/or quantifies human Angiopoietin-like protein 8

(hANGPTL8) in a sample, but does not detect (and/or quantify) hANGPTL3 nor hANGPTL4.

In one embodiment, the subject is human. In another embodiment, the sample is plasma or serum. In further embodiments, the sample is diluted 1:5, 1:10, or 1:50 in PBS or some other known appropriate diluent. In a particular embodiment, the sample is diluted 1:10 in PBS.

In one embodiment, the substrate is selected from a chromogenic substrate, a chemiluminescent substrate, and a chemifluorescent substrate. In another embodiment, the substrate is a chromogenic substrate. In one embodiment, the chromogenic substrate is selected from 2,2'-Azinobis [3-ethylbenzothiazoline-6-sulfonic acid]-diammonium salt (ABTS), 3,3'-Diaminobenzidine (DAB), o-phenylenediamine dihydrochloride (OPD), and 3,3',5,5'-tetramethylbenzidine (TMB). In another embodiment, the chromogenic substrate is p-Nitrophenyl Phosphate, disodium salt (pNPP).

In one embodiment, the capture or detection antibody is selected from the antibodies listed in Table 1. In another embodiment, the capture or detection antibody is selected from H4H15318P, H4H15347P, H4H15361P2, and H4H15341P. In still another embodiment, the capture antibody is H4H15347P or H4H15361P2. In still another embodiment, the detection antibody is H4H15318P.

In another aspect, the invention provides a method for assessing the efficacy or outcome of treating an ANGPTL8-associated disorder in a subject, the method comprising:
Obtaining a sample from a subject;
Adding the sample to the wells of an Enzyme Linked Immunosorbent Assay (ELISA) plate coated with a capture antibody, wherein the capture antibody is a first anti-hANGPTL8 antibody;
Adding a detection antibody to the wells of the plate, wherein the detection antibody is a second anti-hANGPTL8 antibody bound to a tag;
Adding an agent that binds the tag, wherein the agent is conjugated to an enzyme;
Adding a substrate for the enzyme; and
Measuring the amount of product of the enzyme-substrate reaction.

In one embodiment, a decrease in the level of ANGPTL8 in the sample indicates efficacy and/or a positive outcome of the treatment. In another embodiment, the level of ANGPTL8 in the sample assists the clinician in determining whether or not further treatment is warranted.

In another aspect, the invention provides a method for determining whether a subject is at risk for developing an ANGPTL8-associated disorder, the method comprising:
Obtaining a sample from a subject;
Adding the sample to the wells of an Enzyme Linked Immunosorbent Assay (ELISA) plate coated with a capture antibody, wherein the capture antibody is a first anti-hANGPTL8 antibody;
Adding a detection antibody to the wells of the plate, wherein the detection antibody is a second anti-hANGPTL8 antibody bound to a tag;
Adding an agent that binds the tag, wherein the agent is conjugated to an enzyme;
Adding a substrate for the enzyme; and
Measuring the amount of product of the enzyme-substrate reaction.

In one embodiment, an augmented level of ANGPTL8 in the sample indicates risk for developing an ANGPTL8-associated disorder.

In another aspect, the invention provides a method for treating an ANGPTL8-associated disorder in a subject, the method comprising, before, during, and/or after treatment, respectively:
a) Obtaining a sample from a subject;
b) Adding the sample to the wells of an Enzyme Linked Immunosorbent Assay (ELISA) plate coated with a capture antibody, wherein the capture antibody is a first anti-hANGPTL8 antibody;
c) Adding a detection antibody to the wells of the plate, wherein the detection antibody is a second anti-hANGPTL8 antibody bound to a tag;
d) Adding an agent that binds the tag, wherein the agent is conjugated to an enzyme;
e) Adding a substrate for the enzyme; and
f) Measuring the amount of product of the enzyme-substrate reaction;

the method further comprising comparing the amounts measured before, during, and/or after treatment with one another, and continuing or discontinuing treatment based on the comparison. In additional embodiments, a standard curve with known concentrations of hANGPTL8 is generated each time the ELISA is run, and the concentration of hANGPTL8 in the sample is determined using this curve. As a result, the amount of product (measured as optical density) at the end of the ELISA directly correlates to the hANGPTL8 level in the sample.

In one embodiment, a decrease in the level of ANGPTL8 in the sample indicates efficacy and/or a positive outcome of the treatment.

In one aspect, the invention provides a kit for determining if a patient is responsive to treatment of an ANGPTL8-associated disorder/condition, the kit comprising: an Enzyme Linked Immunosorbent Assay (ELISA) plate coated with a capture antibody, wherein the capture antibody is a first anti-hANGPTL8 antibody; a detection antibody, wherein the detection antibody is a second anti-hANGPTL8 antibody bound to a tag, an agent conjugated to an enzyme, a substrate for the enzyme, instructions for obtaining a sample from a subject, and instructions for measuring the amount of ANGPTL8 in the sample.

In another aspect, the invention provides a chromogenic sandwich ELISA assay for detecting and/or determining the level of ANGTPL8, in particular, human ANGPTL8 in a sample, wherein the assay plate wells are coated with a capture antibody (a first anti-hANGPTL8 antibody) before adding the sample (preferably diluted) to the wells; wherein a detection antibody (a second anti-hANGPTL8 antibody bound to a tag) is then added to the wells, followed by an agent conjugated to an enzyme, and then a substrate for the enzyme, allowing for subsequent measurement of the amount of product of the enzyme-substrate reaction. That amount reflects the amount of ANGPTL8 in the sample.

In certain embodiments of a method or kit according to the invention, the capture antibody is H4H15347P, and the detection antibody is H4H15318P.

Other embodiments will become apparent from a review of the ensuing detailed description.

BRIEF DESCRIPTION OF THE FIGURES

FIG. 3C graphically depicts the results of the third mAb pair screen, using H4H15347P as the capture mAb with biotinylated-H4H15318P, and -H4H15341P as the detection mAbs. The upper line (blue in color figure) corresponds to hANGPTL8.mFc.

FIG. 7 graphically depicts the results of serially diluting various ANGPTL proteins in standard curves in order to confirm that the ELISA system described herein is specific for the target antigen, and not for similar proteins.

DETAILED DESCRIPTION

Figure 1:
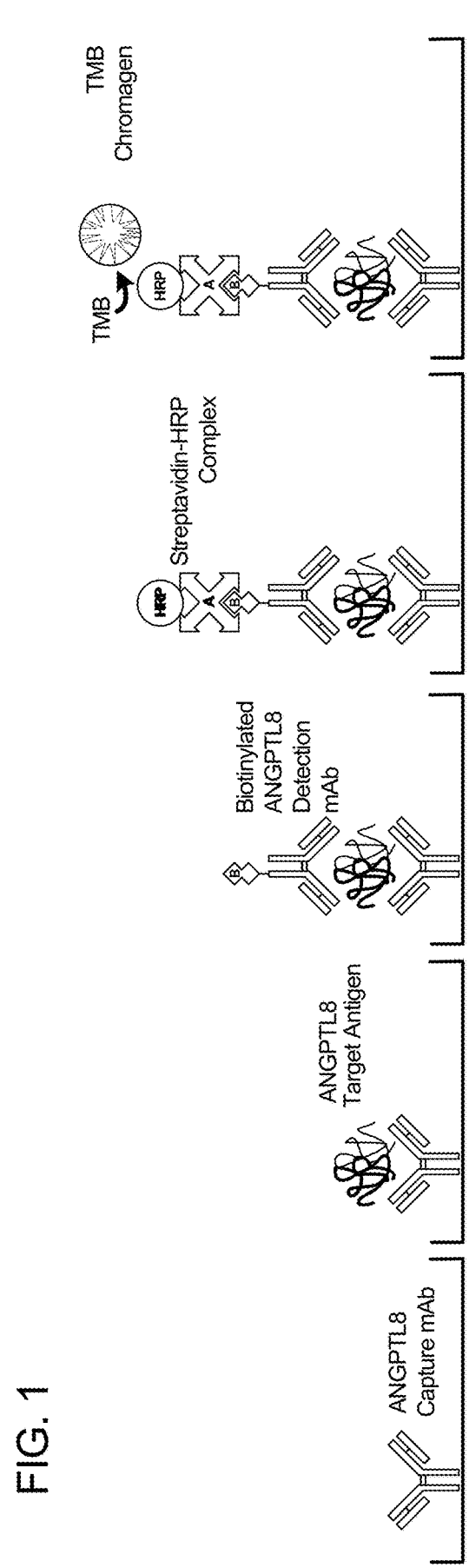
FIG. 1 schematically depicts the basic principle of a chromogenic sandwich ELISA system, as applied to human ANGPTL8.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

"Angiopoietin-like protein 8" or, "ANGPTL8," is a member of the angiopoietin family of proteins, and is sometimes referred to as TD26, RIFL, Lipasin, C19orf80 and Betatrophin. "ANGPTL8", as used herein, refers to human ANGPTL8 comprising the amino acid sequence as set forth in amino acid residues 1-177 of SEQ ID NO: 340. The full-length human ANGPTL8 amino acid sequence, including the signal sequence, can also be found in GenBank accession number NP_061157.3, while the full-length nucleic acid sequence encoding human ANGPTL8 can be found in GenBank accession number NM_018687.6. The N-terminal coiled-coil domain of human ANGPTL8 spans amino acid residues 1-39 of SEQ ID NO: 340 and is also depicted as SEQ ID NO: 337. All references to proteins, polypeptides and protein fragments herein are intended to refer to the human version of the respective protein, polypeptide or protein fragment unless explicitly specified as being from a non-human species. Thus, the expression "ANGPTL8" means human ANGPTL8 unless specified as being from a non-human species, e.g., "mouse ANGPTL8," "monkey ANGPTL8," etc.

The term "human angiopoietin-like protein 3" or "hANGPTL3", as used herein, refers to ANGPTL3 having the nucleic acid sequence shown in SEQ ID NO:343 and the amino acid sequence of SEQ ID NO:342, or a biologically active fragment thereof. The N-terminal coiled-coil domain of human ANGPTL3 is depicted as SEQ ID NO: 338.

The term "human angiopoietin-like protein 4" or "hANGPTL4", as used herein, refers to ANGPTL4 having the nucleic acid sequence shown in SEQ ID NO:345 and the amino acid sequence of SEQ ID NO:344, or a biologically active fragment thereof. The N-terminal coiled-coil domain of human ANGPTL4 is depicted as SEQ ID NO: 339.

As used herein, the expression "anti-ANGPTL8 antibody" includes both monovalent antibodies with a single specificity, as well as bispecific antibodies comprising a first arm that binds ANGPTL8 and a second arm that binds a second (target) antigen, wherein the anti-ANGPTL8 arm comprises any of the HCVR/LCVR or CDR sequences as set forth in Table 1 herein.

The term "antibody", as used herein, means any antigen-binding molecule or molecular complex comprising at least one complementarity determining region (CDR) that specifically binds to or interacts with a particular antigen (e.g., ANGPTL8). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-ANGPTL8 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H^2$—$C_H^3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The term "monoclonal antibody (mAb)", as used herein, is intended to include an antibody specific for a target antigen that is engineered by identical immune cells that are clones from a parent cell.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The antibodies described herein may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. In certain embodiments, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region, which may be desirable, for example, in production, to improve the yield of the desired antibody form.

The antibodies described herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-ANGPTL8 antibodies described herein may comprise one or more amino acid substitutions, insertions and/or deletions in the framework and/or CDR regions of the heavy and light chain variable domains. Such mutations can be readily ascertained by comparing the amino acid sequences disclosed herein to sequences available from, for example, public antibody sequence databases. Once obtained, antibodies and antigen-binding fragments that contain one or more mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The anti-ANGPTL8 antibodies described herein also comprise variants of any of the HCVR, LCVR, and/or CDR amino acid sequences disclosed herein having one or more conservative substitutions. For example, they may have HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

A "blocking antibody" or a "neutralizing antibody", as used herein (or an "antibody that neutralizes ANGPTL8 activity"), is intended to refer to an antibody whose binding to and/or interaction with ANGPTL8 results in inhibition of at least one biological activity of ANGPTL8. For example, an antibody described herein may inhibit the lipoprotein lipase inhibitory activity of ANGPTL8, or it may lower plasma triglycerides through a mechanism other than through inhibition of the LPL inhibitory activity of ANGPTL8. This inhibition of the biological activity of ANGPTL8 can be assessed by measuring one or more indicators of ANGPTL8 biological activity by one or more of several standard in vitro or in vivo assays known in the art. An alternate activity is the triglyceride lowering activity associated with an antibody.

The term "capture mAb" refers to the antibody that is used to coat the wells of the assay plate. It is specific for binding the analyte, or the target antigen (human ANGPTL8 in this system), and immobilizes it from the biological sample.

The term "detection mAb" refers to the antibody that is used to detect levels of the analyte, human ANGPTL8, in the ELISA system described herein. It is conjugated to biotin molecules, in order to utilize the biotin-avidin interaction, when streptavidin is added in the ELISA. This allows for the detection of the target analyte, human ANGPTL8.

"Enzyme-linked immunosorbent assay (ELISA)" is a general plate-based technology used to detect and quantify analytes in various biological samples. In this technique, the analyte is immobilized to a surface (in this case, to an antibody that is attached to the well surface of an assay plate). This analyte is then detected via another antibody specific for it, a detection antibody, which is conjugated to tag molecules.

To measure the "efficacy" or "outcome" of a certain therapy, various clinical measurements are utilized. The "efficacy" or "outcome" of the therapy takes into account several clinical parameters, including a measurement of symptoms (with emphasis on alleviating the symptoms associated with the particular disorder or condition) and the need for concomitant medications. Herein, the efficacy is evaluated in terms of the level of ANGPTL8 in a sample from a subject.

The term "surface plasmon resonance", or "SPR", as used herein, refers to an optical phenomenon that allows for the analysis of real-time biomolecular interactions by detection of alterations in protein concentrations within a biosensor matrix, for example using a BIACORE™ system (Pharmacia Biosensor AB, Uppsala, Sweden and Piscataway, N.J.), or a MASS-1 system (Sierra Sensors, Hamburg, Germany and Greenville, RI).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well known to those of skill in the art. See. e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402, each of which is herein incorporated by reference.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "treating" or "treatment" or "therapy", as used herein, refers to alleviating symptoms, eliminating the causation of symptoms either on a temporary or permanent basis, or preventing or slowing the appearance of symptoms. The term "treating" or "treatment" or "therapy", as used herein, also refers to an approach for obtaining beneficial or desired clinical results. In one embodiment of the invention, a beneficial or desired clinical result includes, but is not limited to, an improvement in blood triglyceride levels, or an improvement in any one or more conditions, diseases, or symptoms associated with, or resulting from, elevated levels of triglycerides, including, but not limited to hypertriglyceridemia, etc. Standard therapy may include fluid administration, or administration of any other pharmaceutical agents useful for lowering blood triglycerides, or lipids, or for weight reduction.

ANGPTL8-associated conditions or disorders (conditions or disorders associated with elevated expression and/or activity of ANGPTL8) that are monitored using methods according to the invention include, without limitation, conditions or diseases associated with, or characterized in part by high blood triglyceride levels, or at least one symptom or complication associated with the condition or disease; hypertriglyceridemia, or at least one symptom associated with hypertriglyceridemia, or risk for acquiring hypertriglyceridemia, for example, in a patient who has a genetic predisposition for developing hypertriglyceridemia, e.g. familial hypertriglyceridemia or familial dysbetalipoproteinemia; any disease or condition improved, ameliorated, inhibited or prevented, (or at least one symptom associated with the disease reduced in severity or frequency of occurrence, compared to that without anti-hANGPTL8 antibody treatment (e.g., ANGPTL8-mediated diseases or disorders), by removing, inhibiting, reducing, or otherwise interfering with, ANGPTL8 activity; diseases or disorders involving lipid metabolism, such as hyperlipidemia, hyperlipoproteinemia and dyslipidemia, including atherogenic dyslipidemia, diabetic dyslipidemia, hypertriglyceridemia, including severe hypertriglyceridemia with TG>1000 mg/dL and associated acute pancreatitis, hypercholesterolemia, chylomicronemia, mixed dyslipidemia (obesity, metabolic syndrome, diabetes, etc.), lipodystrophy, lipoatrophy, and the like, which are caused by, for example, decreased LPL activity and/or LPL deficiency, altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like; diseases or disorders associated with or resulting from triglyceridemia, hypertriglyceridemia, hyperlipidemia, hyper-lipoproteinemia, and/or dyslipidemia, including, but not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like; metabolic syndrome associated dyslipidemia, obesity; other conditions that predispose a patient to high levels of triglycerides, for example, certain medications such as beta blockers, birth control pills, diuretics, steroids, or the use of tamoxifen; conditions, or complications associated with high levels of triglycerides, such as atherosclerosis, stroke, heart attack, and other cardiac conditions; and/or certain other conditions that may lead to high levels of triglycerides, including obesity, poorly controlled diabetes, hypothyroidism, kidney disease, or alcohol consumption.

As used herein, the term "subject" means any human or non-human animal. The terms "subject" and "patient" are used interchangeably herein. As used herein, the term "a subject in need thereof" means any human or non-human animal who: (a) is prone to hypertriglyceridemia and/or other disorders or conditions associated with elevated triglyceride and lipid levels; (b) has previously exhibited symptoms of hypertriglyceridemia and/or other disorders or conditions associated with elevated triglyceride and lipid levels; (c) has a known history of hypertriglyceridemia and/or other disorders or conditions associated with elevated triglyceride and lipid levels; and/or (d) exhibits a sign or symptom of, or is diagnosed as having hypertriglyceridemia and/or other disorders or conditions associated with elevated triglyceride and lipid levels.

The term "sample" or "biological sample" or "subject sample" or "patient sample" may include any tissue sample, including both solid tissue (or extracts thereof), biological fluids, or blood samples. The blood sample may be whole blood, plasma, or serum. The tissue sample or extract thereof, or biological fluid may be any tissue sample or bodily fluid that contains immunoglobulin-expressing cells. In certain embodiments, the sample may require further processing before being added to the inventive ELISA system.

Anti-ANGPTL8 Antibodies

In one embodiment, the antibody employed in the method of the invention is a monoclonal antibody or antigen-binding fragment thereof that specifically binds to ANGPTL8. In another embodiment, the antibody or antigen-binding fragment thereof exhibits one or more of the following characteristics:

a) is a fully human monoclonal antibody;
b) neutralizes, inhibits, blocks, abrogates, reduces, or interferes with at least one activity associated with ANGPTL8;
c) comprises a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 266, 274, 282, 290, 298, 306, 314 and 330;
d) comprises a light chain variable region (LCVR) having an amino acid sequence selected from the group consisting of SEQ ID NO: 10, 26, 42, 58, 74, 90, 106, 122, 138, 154, 170, 186, 202, 218, 234, 250, and 322; or
e) cross-competes with a reference antibody, wherein the reference antibody comprises a heavy chain variable region (HCVR) and a light chain variable region (LCVR) amino acid sequence selected from the group consisting of any of the HCVR and LCVR amino acid sequences of Table 1.

Fully human antibodies specific for ANGPTL8 have been described that may be used in a clinical setting to treat diseases, or conditions characterized by elevated levels of triglycerides, including hypertriglyceridemia (U.S. Pat. No. 9,018,356, incorporated herein in its entirety). Methods for generating monoclonal antibodies, including fully human monoclonal antibodies are known in the art.

VELOCIMMUNE® technology (see, for example, U.S. Pat. No. 6,596,541, Regeneron Pharmaceuticals, VELOCIMMUNE®) or any other known method for generating monoclonal antibodies can be used to initially isolate high affinity chimeric antibodies to an allergen having a human variable region and a mouse constant region, as described in U.S. Pat. No. 9,018,356. As further described therein, the high affinity chimeric antibodies, which are isolated having a human variable region and a mouse constant region, are characterized and selected for desirable characteristics, including affinity, selectivity, epitope, etc. The mouse constant regions are then replaced with a desired human constant region to generate the fully human antibody of the invention, for example wild-type or modified IgG1 or IgG4. While the constant region selected may vary according to specific use, high affinity antigen binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase.

Exemplary anti-ANGPTL8 antibodies are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of exemplary anti-ANGPTL8 antibodies. Table 2 sets forth the nucleic acid sequence identifiers of the HCVRs, LCVRs, HCDR1, HCDR2 HCDR3, LCDR1, LCDR2 and LCDR3 of the exemplary anti-ANGPTL8 antibodies.

The inventive method employs, as capture and/or detection antibodies, antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The inventive method also employs, as capture and/or detection antibodies, antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The inventive method also employs, as capture and/or detection antibodies, antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1.

In one embodiment, the method employs, as capture and/or detection antibodies, an isolated antibody or antigen-binding fragment thereof that binds specifically to and/or inhibits at least one activity associated with ANGPTL8, wherein the antibody or antigen-binding fragment comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

In another embodiment, the method employs, as capture and/or detection antibodies, an isolated antibody or antigen-binding fragment thereof that binds specifically to and/or inhibits at least one activity associated with ANGPTL8, wherein the antibody or antigen-binding fragment comprises a HCVR/LCVR amino acid sequence pair selected from the group consisting of SEQ ID NOs: 34/42, 162/170, 226/234, and 290/250.

In one embodiment, the inventive method employs, as capture and/or detection antibodies, an isolated antibody or antigen-binding fragment thereof that binds to and/or inhibits at least one activity associated with ANGPTL8, wherein the antibody or antigen-binding fragment comprises: (a) three heavy chain complementarity determining regions (CDRs) (HCDR1, HCDR2 and HCDR3) contained within any one of the heavy chain variable region (HCVR) sequences as set forth in Table 1; and (b) three light chain CDRs (LCDR1, LCDR2 and LCDR3) contained within any one of the light chain variable region (LCVR) sequences as set forth in Table 1.

In one embodiment, the method employs, as capture and/or detection antibodies, an isolated antibody or antigen-binding fragment thereof that binds specifically to and/or inhibits at least one activity associated with ANGPTL8, wherein the antibody or antigen-binding fragment comprises:
  (a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 268, 276, 284, 292, 300, 308, 316 and 332;
  (b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 270, 278, 286, 294, 302, 310, 318, and 334;
  (c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 272, 280, 288, 296, 304, 312, 320 and 336;
  (d) a LCDR1 domain having an amino acid sequence selected from the group consisting of SEQ ID NOs: 12, 28, 44, 60, 76, 92, 108, 124, 140, 156, 172, 188, 204, 220, 236, 252 and 324;
  (e) a LCDR2 domain having an amino acid sequence selected from the group consisting of SEQ ID NOs: 14, 30, 46, 62, 78, 94, 110, 126, 142, 158, 174, 190, 206, 222, 238, 254, and 326; and
  (f) a LCDR3 domain having an amino acid sequence selected from the group consisting of SEQ ID NOs: 16, 32, 48, 64, 80, 96, 112, 128, 144, 160, 176, 192, 208, 224, 240, 256 and 328.

The inventive method also employs, as capture and/or detection antibodies, antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The inventive method also employs, as capture and/or detection antibodies, antibodies or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The inventive method also employs, as capture and/or detection antibodies, antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The inventive method also employs, as capture and/or detection antibodies, antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The inventive method also employs, as capture and/or detection antibodies, antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The inventive method also employs, as capture and/or detection antibodies, antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The inventive method also employs, as capture and/or detection antibodies, antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the inventive method also employs, as capture and/or detection antibodies, antibodies, or antigen-binding fragments thereof, comprising an HCDR3/LCDR3 amino acid sequence pair contained within any of the exemplary anti-ANGPTL8 antibodies listed in Table 1.

The inventive method also employs, as capture and/or detection antibodies, antibodies, or antigen-binding fragments thereof, comprising a set of six CDRs (i.e., HCDR1-HCDR2-HCDR3-LCDR1-LCDR2-LCDR3) contained within any of the exemplary anti-ANGPTL8 antibodies listed in Table 1. In certain embodiments, the HCDR1-HCDR2-HCDR3-LCDR1-LCDR2-LCDR3 amino acid sequence set is selected from the group consisting of SEQ ID NOs: 36-38-40-44-46-48 (e.g., H4H15318P); 164-166-168-172-174-176 (e.g., H4H15341P); 228-230-232-236-238-240 (e.g., H4H15347P); 292-294-296-252-254-256 (e.g., H4H15361P2).

The inventive method also employs, as capture and/or detection antibodies, antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-ANGPTL8 antibodies listed in Table 1. For example, the inventive method also employs, as capture and/or detection antibodies, antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 34/42 (e.g., H4H15318P), 162/170 (e.g., H4H15341P), 226/234 (e.g., H4H15347P), and 290/250 (e.g., H4H15361P2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The inventive method also employs, as capture and/or detection antibodies, antibodies and antigen-binding fragments thereof that compete for specific binding to ANGPTL8 with a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the inventive method employs, as capture and/or detection antibodies, an isolated monoclonal antibody or antigen-binding fragment thereof that competes for binding to ANGPTL8 with a reference antibody comprising an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

The inventive method also employs, as capture and/or detection antibodies, antibodies and antigen-binding fragments thereof that bind the same epitope on ANGPTL8 as a reference antibody or antigen-binding fragment thereof comprising the CDRs of a HCVR and the CDRs of a LCVR, wherein the HCVR and LCVR each has an amino acid sequence selected from the HCVR and LCVR sequences listed in Table 1.

In one embodiment, the inventive method employs, as capture and/or detection antibodies, an isolated monoclonal antibody or antigen-binding fragment thereof that binds to the same epitope on ANGPTL8 as a reference antibody comprising an HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

In one embodiment, the inventive method employs, as capture and/or detection antibodies, an isolated antibody that binds specifically to and/or inhibits at least one activity associated with ANGPTL8, and that is a recombinantly produced human monoclonal antibody.

In one embodiment, the inventive method employs, as capture and/or detection antibodies, an isolated antibody that binds specifically to and/or inhibits at least one activity associated with ANGPTL8, and that is a recombinantly produced human monoclonal antibody having a HCVR and/or an LCVR sequence selected from the amino acid sequences found in Table 1.

In one embodiment, the inventive method employs, as capture and/or detection antibodies, an isolated antibody that binds specifically to and/or inhibits at least one activity associated with ANGPTL8, and that is a recombinantly produced human monoclonal antibody having a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/250, 266/250, 274/250, 282/250, 290/250, 306/250, 314/322, and 330/322.

The inventive method also employs, as capture and/or detection antibodies, an isolated antibody that binds specifically to and/or inhibits at least one activity associated with ANGPTL8, and that is a recombinantly produced human monoclonal antibody having a HCVR and/or a LCVR encoded by a nucleic acid sequence selected from the nucleic acid sequences found in Table 2.

The inventive method also employs, as capture and/or detection antibodies, anti-ANGPTL8 antibodies that bind to the same epitope as any of the specific exemplary antibodies described herein (e.g. antibodies comprising any of the amino acid sequences as set forth in Table 1 herein). Likewise, the inventive method employs, as capture and/or detection antibodies, anti-ANGPTL8 antibodies that compete for binding to ANGPTL8 with any of the specific exemplary antibodies described herein (e.g. antibodies comprising any of the amino acid sequences as set forth in Table 1 herein).

One can easily determine whether an antibody binds to the same epitope as, or competes for binding with, a reference anti-ANGPTL8 antibody by using routine methods known in the art and exemplified herein. For example, to determine if a test antibody binds to the same epitope as a reference anti-ANGPTL8 antibody of the invention, the reference antibody is allowed to bind to an ANGPTL8 protein. Next, the ability of a test antibody to bind to the ANGPTL8 molecule is assessed. If the test antibody is able to bind to ANGPTL8 following saturation binding with the reference anti-ANGPTL8 antibody, it can be concluded that the test antibody binds to a different epitope than the reference anti-ANGPTL8 antibody. On the other hand, if the test antibody is not able to bind to the ANGPTL8 molecule following saturation binding with the reference anti-ANGPTL8 antibody, then the test antibody may bind to the same epitope as the epitope bound by the reference anti-ANGPTL8 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-ANGPTL8 antibody, the above-described binding methodology is performed in two orientations: In a first orientation, the reference antibody is allowed to bind to a ANGPTL8 protein under saturating conditions followed by assessment of binding of the test antibody to the ANGPTL8 molecule. In a second orientation, the test antibody is allowed to bind to an ANGPTL8 molecule under saturating conditions followed by assessment of binding of the reference antibody to the ANGPTL8 molecule. If, in both orientations, only the first (saturating) antibody is capable of binding to the ANGPTL8 molecule, then it is concluded that the test antibody and the reference antibody compete for binding to ANGPTL8. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Uses of the Inventive ELISA Assay System

In one embodiment, by allowing the clinician monitoring or treating a patient to assess ANGPTL8 levels in the patient, the methods described herein may be used to prevent the onset of a disease or disorder characterized in part by elevated blood triglyceride levels, or to prevent the likelihood of developing such disease or disorder, or to mitigate the severity of the disease or disorder, or at least one symptom associated with the disease or disorder, or to prevent long term complications associated with a disease characterized by high triglyceride levels.

In one embodiment, the method of the invention may be used in assessing the need for or efficacy of a medicament for treating any disease or disorder characterized in part by elevated levels of triglycerides.

The method of the invention may be used to monitor progress in short-term therapy in an acute setting, or in long-term use as chronic therapy.

Sandwich ELISA

Principle of Assay

In a basic chromogenic sandwich ELISA, the wells of an assay plate are coated with a capture antibody that is specific for the target antigen of interest. The capture antibody is immobilized on the well surface. Samples are then added, where the target antigen binds to the antibody coating the well. Next, another antibody that is specific for the target antigen is added, and also binds to the immobilized target antigen. This detection antibody is bound to a tag, usually biotin. Streptavidin conjugated to horseradish peroxidase (HRP) is then applied. Having high affinity for biotin, streptavidin binds to biotin in the complex. When 3,3',5,5'-Tetramethylbenzidine (TMB), the substrate for HRP, is added, an enzymatic reaction occurs. The products of this reaction are quantified by reading the absorbance with a spectrophotometer. (FIG. 1).

Exemplary Materials and Equipment

In certain embodiments, reagents employed include: as capture mAb: anti-human C19orf80 (ANGPTL8) (H4H15347P), as capture mAb: anti-human C19orf80 (ANGPTL8) (H4H15361P2); as detection mAb: biotinylated anti-human C19orf80 (ANGPTL8) (biotin-H4H15318P); as protein standard: untagged human ANGPTL8 protein (outsourced); as protein standard: human ANGPTL8 dimer protein with mouse Fc tag; as protein standard: human ANGPTL8 monomer protein with myc-myc-his tag.

Additional reagents employed in certain embodiments include: Phosphate-buffered saline (PBS), 1×, pH 7.2; Fraction V bovine serum albumin (BSA); Blocking buffer: 1% Fraction V BSA in PBS; TWEEN® 20/Tween 20™ nonionic detergent; Assay diluent: 1% Fraction V BSA/0.1% TWEEN® 20/Tween 20™ in PBS; Wash buffer: 0.1% TWEEN® 20/Tween 20™ in PBS; 3,3',5,5'-Tetramethyl-benzidine liquid substrate (TMB); 2 Normal sulfuric acid; Horseradish peroxidase-conjugated streptavidin (streptavidin-HRP).

Instruments and Labware employed in certain embodiments include: 96-well, clear, high-binding surface assay plates; Biotek EL406 plate washer dispenser with accompanying Liquid Handling Control software; Molecular Devices SpectraMax i3 microplate reader system with accompanying SoftMax Pro application (version 6.3.1).

Assay Procedure

Proteins and mAbs stored at −80° C. were thawed and kept on ice, as they were needed. The wells of the ELISA plate were coated with capture mAb, at a concentration of 4 µg/mL in PBS, and a volume of 100 µL/well. The plate was covered with a plate sealer, and stored at 4° C. overnight (approximately 18 hours). The wells of the plate were then washed with 350 µL/well wash buffer (0.1% TWEEN® 20/Tween 20™ in PBS), for a total of 3 washes, using an automated plate washer. Excess wash remnants were removed by inverting and tapping the plate against clean paper towels. Blocking buffer (1% Fraction V BSA in PBS) was added at 300 µL/well. The plate was covered with a plate sealer, and placed on a plate shaker at room temperature, shaking at 300 rpm for a minimum of 1 hour.

During this period of blocking, the standard curves and samples were prepared for duplicate in the ELISA. The standard curve dilutions were typically prepared in U-bottom dilution plates, where the most concentrated standard was prepared at 200 ng/mL in PBS, and then serially-diluted 2-fold, to generate a 12-point curve, where the final point is the blank (PBS only) at Ong/mL protein. Enough volume of each concentration was prepared to assay in duplicate wells, with 100 µL/well. Serum or plasma samples require troubleshooting in order to determine the proper dilution in PBS so as to obtain absorbance values that lie within the linear range of the standard curve. Typically, several dilutions were made in PBS in U-bottom dilution plates.

After the blocking period, the wells of the ELISA plate were washed again, and excess wash remnants were removed, as previously described. The standards and the diluted samples were added to the plate in duplicate, with 100 µL/well. The plate was covered with a plate sealer and placed on a plate shaker at room temperature, shaking at 500 rpm for 2 hours. The wells of the ELISA plate were washed again, and excess wash remnants were removed, as previously described. The detection mAb was added at a concentration of 400 ng/mL in assay diluent (1% Fraction V BSA/0.1% TWEEN® 20/Tween 20™ in PBS), with 150 µL/well. The plate was covered with a plate sealer and placed on a plate shaker at room temperature, shaking at 500 rpm for 1 hour. The wells of the ELISA plate were washed again, and excess wash remnants were removed, as previously described. Horseradish peroxidase-conjugated streptavidin was added at a concentration of 100 ng/mL in assay diluent, with 150 µL/well. The plate was covered with a plate sealer and placed on a plate shaker at room temperature, shaking at 500 rpm for 30 minutes. The wells of the ELISA plate were washed again, as previously described, but 4 times, and excess wash remnants were removed. 3,3',5,5'-Tetramethylbenzidine liquid substrate (TMB) was added at 100 µL/well. The plate was covered with a plate sealer, and protected from light, covered with aluminum foil. The plate was placed on a plate shaker at room temperature, shaking for approximately 15 minutes. As the liquid in the wells of the assay plate turned from clear to blue in color during this incubation period, the color was carefully monitored so as to avoid undersaturation and oversaturation of substrate. Sulfuric acid (2N) was added to each well at 100 µL/well in order to stop the reaction. The bottom of the plate was quickly wiped with ethanol in order to remove any possible remnant contamination that may affect the reading of the plate by spectrophotometry. The plate was read immediately, at most within 15 minutes of adding the stop solution, using a spectrophotometric plate reader, set to 450 nm, with a wavelength correction set to 540 nm.

Data Analysis

The data obtained in SoftMax Pro file format were exported to Microsoft Excel, where wavelength correction was calculated by subtracting the absorbance reading at 540 nm from the absorbance reading at 450 nm. These true optical density values were then transferred to GraphPad Prism, where wells were masked on a need basis. Standard curves were generated, using nonlinear, 3-parameter Hills equation curve fit. Optical density values of samples that fell within the linear range of the appropriate standard curve were transformed in order to account for dilution factor of the loaded sample.

Detection Strategies for ELISA System

The final stage in the ELISA system is the detection/measurement step, after an enzyme substrate is introduced (unless a radioactive or fluorescent tag was used). The substrate is converted to a detectable product by the enzyme. The intensity of signal produced when the substrate is added is directly proportional to the amount of hANGPTL8 captured in the plate and bound by the detection antibodies. Thus, enzyme-conjugated antibodies (for example, with horseradish peroxidase, HRP) offer flexibility in the instant ELISA detection/measurement method because of the myriad substrates available for chromogenic, chemifluorescent and chemiluminescent imaging.

Chromogenic ELISA substrates allow direct visualization and are detected with standard absorbance plate readers common to many laboratories. HRP catalyzes the conversion of chromogenic substrates (e.g., TMB, OPD, DAB, ABTS) into colored products; it can be conjugated to a labeled molecule. HRP produces a colored derivative of the labeled molecule when incubated with a proper substrate, allowing it to be detected and quantified. HRP is often used in conjugates to determine the presence of a molecular target. It is commonly used in ELISA systems due to its monomeric nature and the ease with which it produces colored products.

Chemifluorescent ELISA substrates are for use with a fluorescent plate reader.

Chemiluminescent ELISA substrates are for use with a luminometer or other plate reader that can measure total luminescence.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described. All publications mentioned herein are incorporated herein by reference in their entirety.

Example 1. Selection of Purified Candidate mAbs to Use as Pairs in ELISA-Based System for Determination of Human ANGPTL8 Levels Anti-ANGPTL8 antibodies were obtained by immunizing a VELOCIMMUNE® mouse (i.e., an engineered mouse comprising DNA encoding human immunoglobulin heavy and kappa light chain variable regions) with an immunogen comprising a recombinant human ANGPTL8 expressed with a C-terminal mouse IgG2a tag (See SEQ ID NO: 340). The antibody immune response was monitored by an ANGPTL8-specific immunoassay. When a desired immune response was achieved, several fully human anti-ANGPTL8 antibodies we generated from antigen-positive B cells as described in US 2007/0280945A1, incorporated by reference herein in its entirety.

Table 1 sets forth the amino acid sequence identifiers of the heavy and light chain variable regions and CDRs of selected anti-ANGPTL8 antibodies utilized in the assay described herein. The corresponding nucleic acid sequence identifiers are set forth in Table 2.

TABLE 1

| | Amino Acid Sequence Identifiers SEQ ID NOs: | | | | | | | |
|---|---|---|---|---|---|---|---|---|
| Antibody Designation | HCVR | HCDR1 | HCDR2 | HCDR3 | LCVR | LCDR1 | LCDR2 | LCDR3 |
| H4H15314P2 | 2 | 4 | 6 | 8 | 10 | 12 | 14 | 16 |
| H4H15316P | 18 | 20 | 22 | 24 | 26 | 28 | 30 | 32 |
| H4H15318P | 34 | 36 | 38 | 40 | 42 | 44 | 46 | 48 |
| H4H15319P | 50 | 52 | 54 | 56 | 58 | 60 | 62 | 64 |
| H4H15321P | 66 | 68 | 70 | 72 | 74 | 76 | 78 | 80 |
| H4H15323P | 82 | 84 | 86 | 88 | 90 | 92 | 94 | 96 |
| H4H15330P | 98 | 100 | 102 | 104 | 106 | 108 | 110 | 112 |
| H4H15331P | 114 | 116 | 118 | 120 | 122 | 124 | 126 | 128 |
| H4H15334P | 130 | 132 | 134 | 136 | 138 | 140 | 142 | 144 |

TABLE 1-continued

Amino Acid Sequence Identifiers
SEQ ID NOs:

| Antibody Designation | HCVR | HCDR1 | HCDR2 | HCDR3 | LCVR | LCDR1 | LCDR2 | LCDR3 |
|---|---|---|---|---|---|---|---|---|
| H4H15335P | 146 | 148 | 150 | 152 | 154 | 156 | 158 | 160 |
| H4H15341P | 162 | 164 | 166 | 168 | 170 | 172 | 174 | 176 |
| H4H15343P | 178 | 180 | 182 | 184 | 186 | 188 | 190 | 192 |
| H4H15345P | 194 | 196 | 198 | 200 | 202 | 204 | 206 | 208 |
| H4H15346P | 210 | 212 | 214 | 216 | 218 | 220 | 222 | 224 |
| H4H15347P | 226 | 228 | 230 | 232 | 234 | 236 | 238 | 240 |
| H4H15350P2 | 242 | 244 | 246 | 248 | 250 | 252 | 254 | 256 |
| H4H15353P2 | 258 | 260 | 262 | 264 | 250 | 252 | 254 | 256 |
| H4H15354P2 | 266 | 268 | 270 | 272 | 250 | 252 | 254 | 256 |
| H4H15355P2 | 274 | 276 | 278 | 280 | 250 | 252 | 254 | 256 |
| H4H15357P2 | 282 | 284 | 286 | 288 | 250 | 252 | 254 | 256 |
| H4H15361P2 | 290 | 292 | 294 | 296 | 250 | 252 | 254 | 256 |
| H4H15362P2 | 298 | 300 | 302 | 304 | 250 | 252 | 254 | 256 |
| H4H15363P2 | 306 | 308 | 310 | 312 | 250 | 252 | 254 | 256 |
| H4H15367P2 | 314 | 316 | 318 | 320 | 322 | 324 | 326 | 328 |
| H4H15369P2 | 330 | 332 | 334 | 336 | 322 | 324 | 326 | 328 |

TABLE 2

Nucleic Acid Sequence Identifiers
SEQ ID NOs:

| Antibody Designation | HCVR | HCDR1 | HCDR2 | HCDR3 | LCVR | LCDR1 | LCDR2 | LCDR3 |
|---|---|---|---|---|---|---|---|---|
| H4H15314P2 | 1 | 3 | 5 | 7 | 9 | 11 | 13 | 15 |
| H4H15316P | 17 | 19 | 21 | 23 | 25 | 27 | 29 | 31 |
| H4H15318P | 33 | 35 | 37 | 39 | 41 | 43 | 45 | 47 |
| H4H15319P | 49 | 51 | 53 | 55 | 57 | 59 | 61 | 63 |
| H4H15321P | 65 | 67 | 69 | 71 | 73 | 75 | 77 | 79 |
| H4H15323P | 81 | 83 | 85 | 87 | 89 | 91 | 93 | 95 |
| H4H15330P | 97 | 99 | 101 | 103 | 105 | 107 | 109 | 111 |
| H4H15331P | 113 | 115 | 117 | 119 | 121 | 123 | 125 | 127 |
| H4H15334P | 129 | 131 | 133 | 135 | 137 | 139 | 141 | 143 |
| H4H15335P | 145 | 147 | 149 | 151 | 153 | 155 | 157 | 159 |
| H4H15341P | 161 | 163 | 165 | 167 | 169 | 171 | 173 | 175 |
| H4H15343P | 177 | 179 | 181 | 183 | 185 | 187 | 189 | 191 |
| H4H15345P | 193 | 195 | 197 | 199 | 201 | 203 | 205 | 207 |
| H4H15346P | 209 | 211 | 213 | 215 | 217 | 219 | 221 | 223 |
| H4H15347P | 225 | 227 | 229 | 231 | 233 | 235 | 237 | 239 |
| H4H15350P2 | 241 | 243 | 245 | 247 | 249 | 251 | 253 | 255 |
| H4H15353P2 | 257 | 259 | 261 | 263 | 249 | 251 | 253 | 255 |
| H4H15354P2 | 265 | 267 | 269 | 271 | 249 | 251 | 253 | 255 |
| H4H15355P2 | 273 | 275 | 277 | 279 | 249 | 251 | 253 | 255 |
| H4H15357P2 | 281 | 283 | 285 | 287 | 249 | 251 | 253 | 255 |
| H4H15361P2 | 289 | 291 | 293 | 295 | 249 | 251 | 253 | 255 |
| H4H15362P2 | 297 | 299 | 301 | 303 | 249 | 251 | 253 | 255 |
| H4H15363P2 | 305 | 307 | 309 | 311 | 249 | 251 | 253 | 255 |
| H4H15367P2 | 313 | 315 | 317 | 319 | 321 | 323 | 325 | 327 |
| H4H15369P2 | 329 | 331 | 333 | 335 | 321 | 323 | 325 | 327 |

Antibodies are typically referred to herein according to the following nomenclature: Fc prefix (e.g. "H1H," "H1M," "H2M", "H4H", etc.), followed by a numerical identifier (e.g. "15321," "15341," "15350," etc.), followed by a "P" or "N" suffix as shown in Tables 1 and 2. Thus, according to this nomenclature, an antibody may be referred to herein as, e.g., "H4H15321P", etc. The H4H prefix on the antibody designations used herein indicate the particular Fc region isotype of the antibody. For example, an "H4H" antibody has a human IgG4 Fc, an "H1M" antibody has a mouse IgG1 Fc, and an "H2M" antibody has a mouse IgG2 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

In order for an ELISA method of protein detection and quantification to be reliable, there is a need for quality capture and detection mAbs that can recognize the target analyte in biological samples. This initial step was executed in order to select potential capture mAbs and detection mAbs that are able to target and bind to the human ANGPTL8 analyte in the ELISA system.

Figure 2:
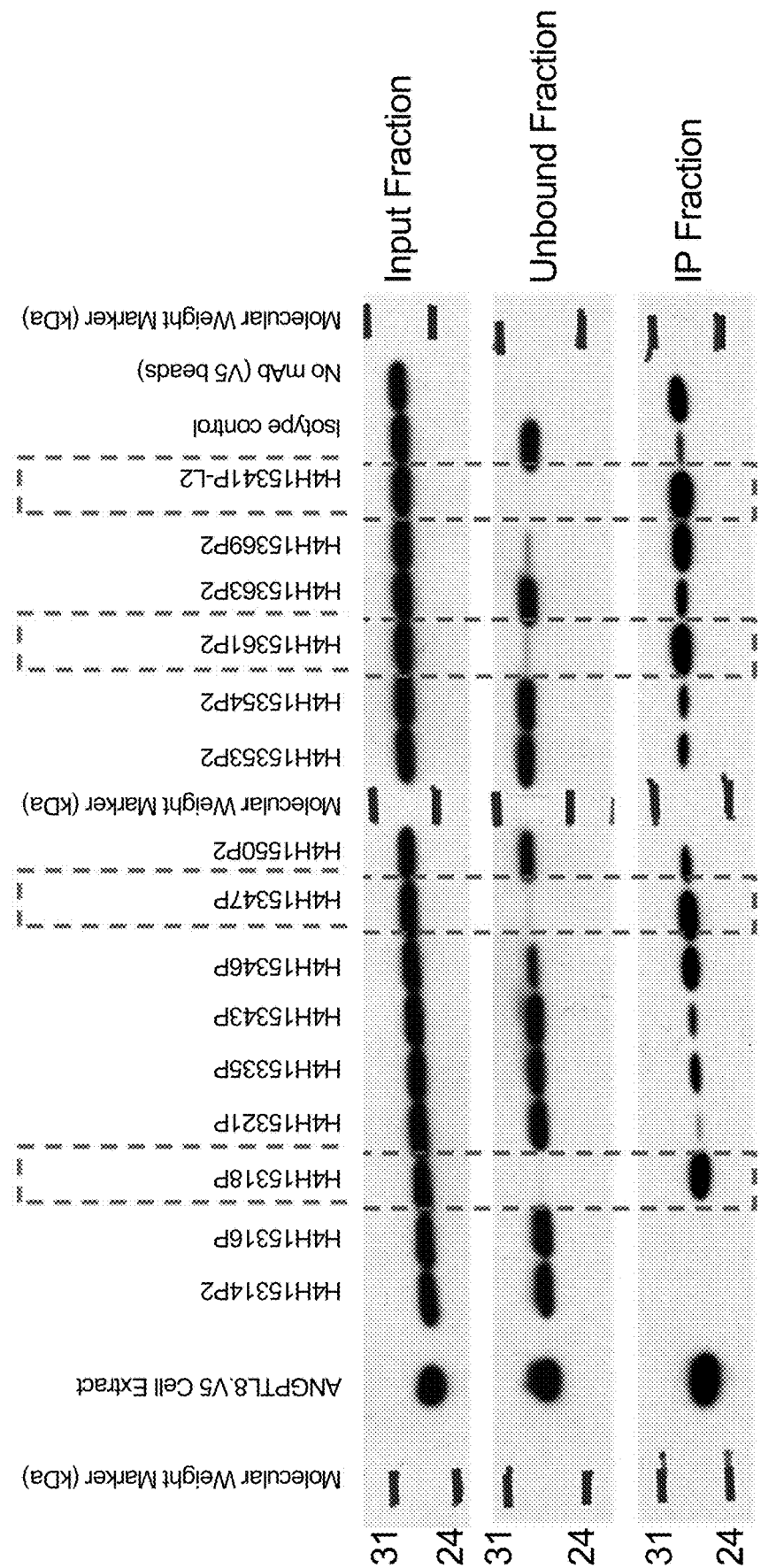
FIG. 2 shows an immunoblot providing the results of the immunoprecipitations that tested the ability of each instantly purified human ANGPTL8 mAb to pull down human ANGPTL8 protein from cell-conditioned media.

The selection process involved performing a series of immunoprecipitations (IPs), in which each mAb was incubated with cell conditioned media (CM) containing the human ANGPTL8 protein. A resin that identifies human IgG4 was then applied to the mAb/CM mixtures. The resin beads targeted the mAbs, binding the mAb-human ANGPTL8 complex. A series of Western blots probing for human ANGPTL8 were run on the various fractions of the IPs, and anti-human ANGPTL8 mAbs were selected based on high human ANGPTL8 expression in the IP fractions, with low human ANGPTL8 expression in the unbound fractions.

mAbs found to strongly and specifically bind human ANGPTL8 in the immunoprecipitated fractions, with minimal human ANGPTL8 protein detected in the unbound fractions, included: H4H15318P, H4H15347P, H4H15361P2, and H4H15341P (FIG. 2). Therefore, these four mAbs were selected to be tested in the ELISA, with each as the capture mAb and each as the biotinylated detection mAb.

Example 2: Evaluation of Various Combinations of Candidate Capture mAbs and Detection mAbs in ELISA; Determination of Proper Purified Human ANGPTL8 Protein to Use as ELISA Standard; Testing of Native Condition Versus Denatured Condition of Human ANGPTL8 Standard Protein in Human ANGPTL8 Detection This series of ELISAs had a three-fold purpose: (1) to select which pair of candidate capture and detection mAbs performed best in the ELISA; (2) to test both a monomer form and a dimer form of the human ANGPTL8 protein as a standard protein; (3) to test whether native condition or acid-denatured condition of the human ANGPTL8 protein enables stronger detection of ANGPTL8.

Each of the four selected candidate mAbs was tested as a capture mAb and as a detection mAb, forming possible pairs. Each possible mAb pair was tested using both the monomer and the dimer forms of human ANGPTL8 as the standard protein, to generate a standard curve, using a 10-point, 2-fold serial dilution series, ranging from 50 ng/mL-0ng/mL. Each possible mAb pair, with each form of human ANGPTL8 standard was tested under both native condition and acid-denatured condition.

Figure 3A:
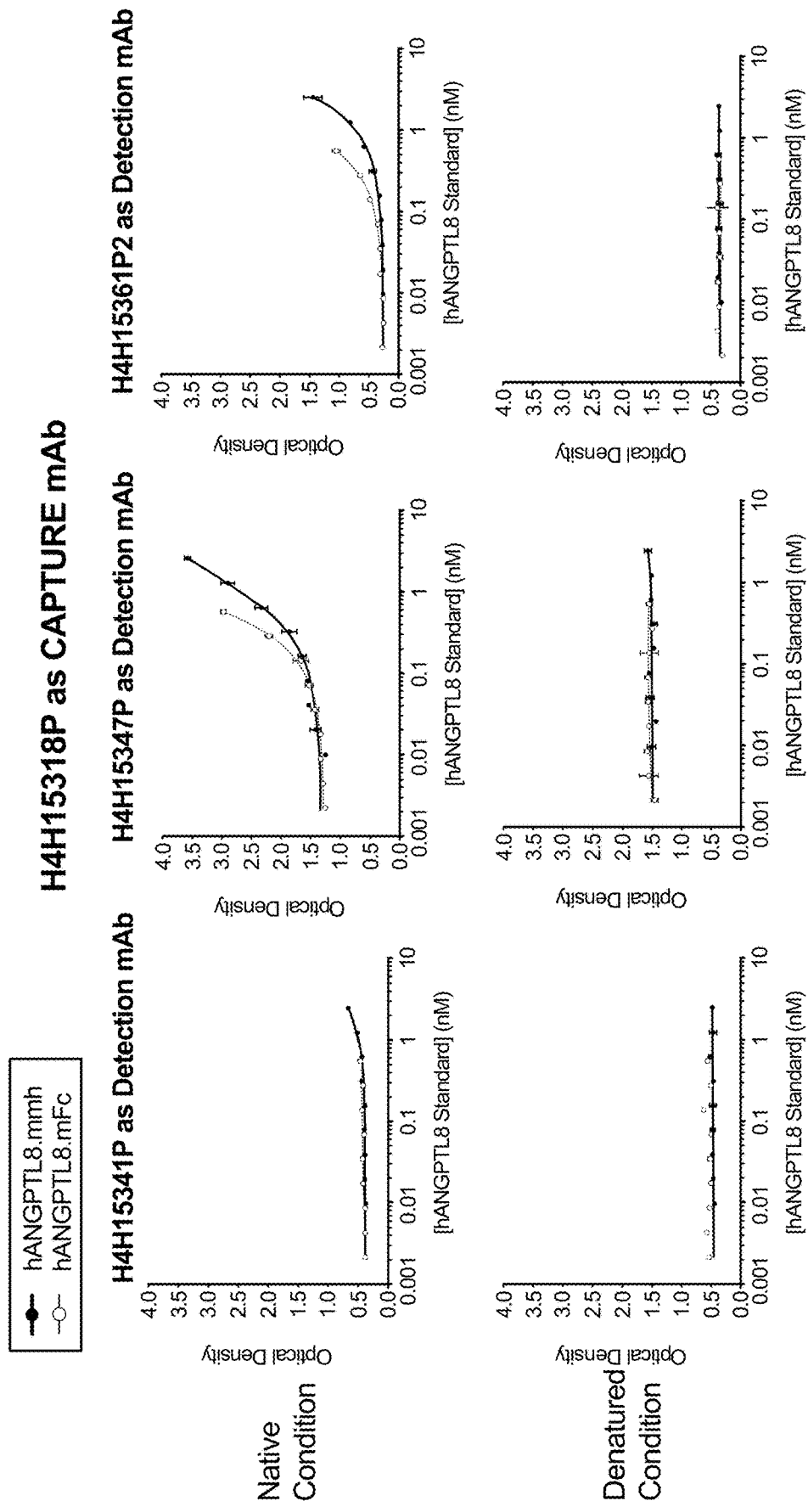
FIG. 3A graphically depicts the results of the first mAb pair screen, using H4H15318P as the capture mAb with biotinylated-H4H15341P, -H4H15347P, and -H4H15361P2 as the detection mAbs. The upper line (blue in color figure) corresponds to hANGPTL8.mFc.
Figure 3B:
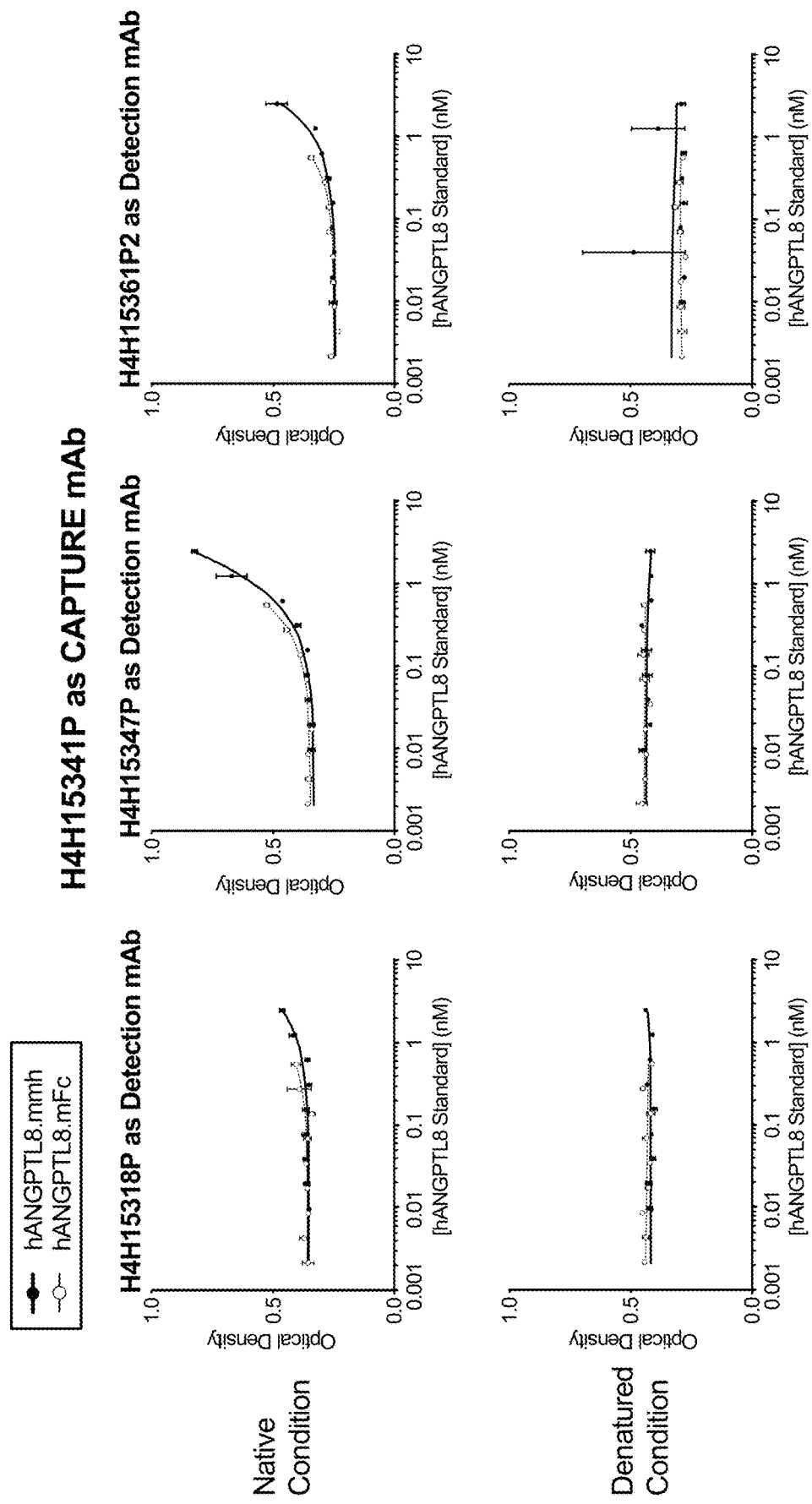
FIG. 3B graphically depicts the results of the second mAb pair screen, using H4H15341P as the capture mAb with biotinylated-H4H15318P, -H4H15347P, and -H4H15361P2 as the detection mAbs. The upper line (blue in color figure) (except in lower right-hand corner graph, where it is the lower line) corresponds to hANGPTL8.mFc.
Figure 3D:
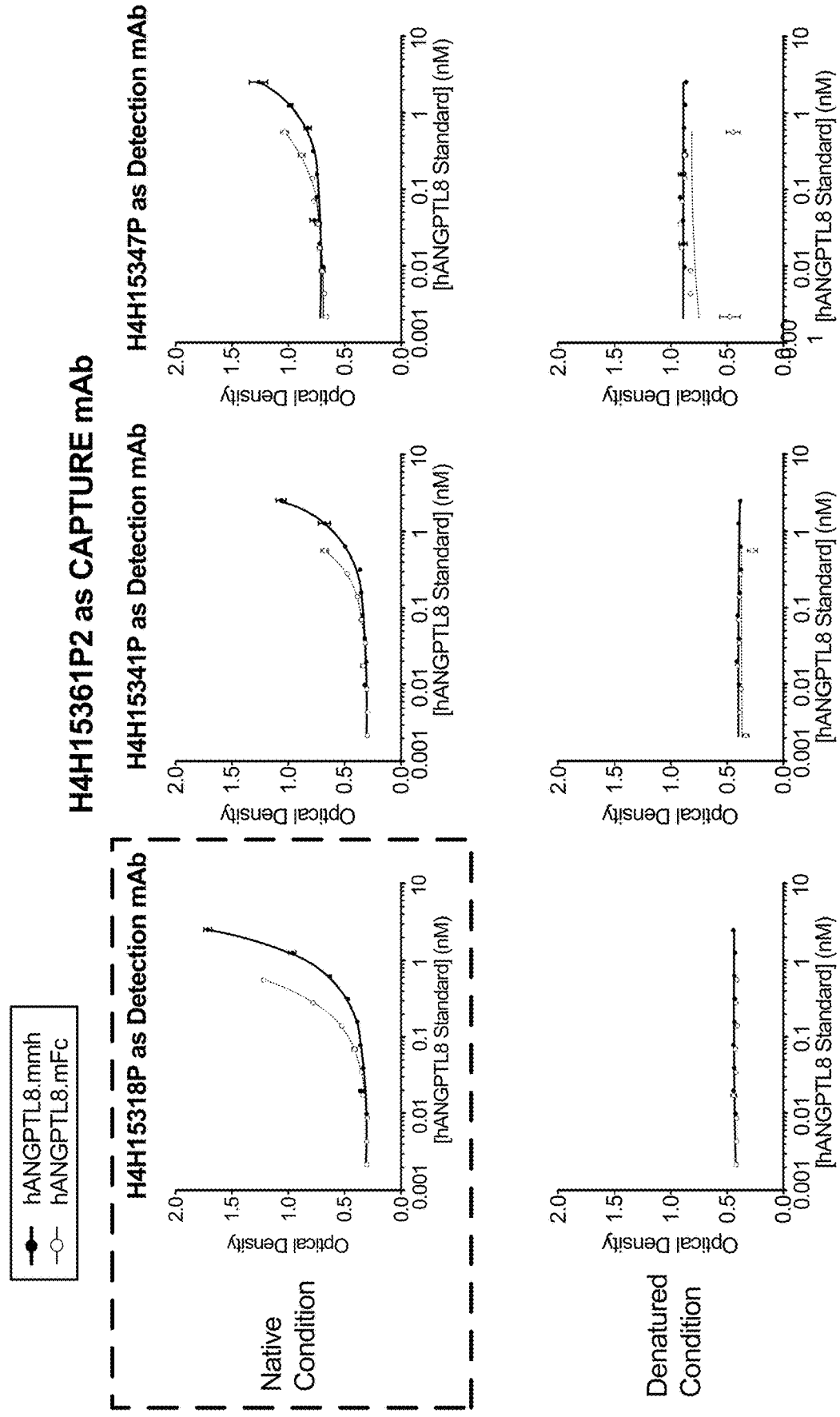
FIG. 3D graphically depicts the results of the fourth mAb pair screen, using H4H15361P2 as the capture mAb with biotinylated-H4H15318P, -H4H15341P, and -H4H15347P as the detection mAbs. The upper line (blue in color figure) (except in lower three graphs, where it is the lower line) corresponds to hANGPTL8.mFc.

Both H4H15347P and H4H15361P2 performed best as the capture mAbs, while biotin-H4H15318P performed best as a detection mAb, with the selected capture mAbs. The monomer form of human ANGPTL8 protein produced better standard curves, with wider linear ranges, and with more points in the linear range. Human ANGPTL8 is detectable under native conditions, and undetectable under acid-denatured conditions, using the purified mAbs and proteins listed herein (FIG. 3).

Example 3: Comparison of Human ANGPTL8 Detection in Ex Vivo Serum Samples, Using Selected Purified Candidate mAb Pairs It is crucial that the ELISA platform, using the selected capture and detection mAbs, is able to detect human ANGPTL8 protein in various types of biological samples that contain the protein. At the same time, it is also important that the ELISA described herein shows specificity for the target analyte, by not detecting it in samples from a different species. This study evaluated the specificity of the selected human ANGPTL8 capture and detection mAbs in the ELISA, using various ex vivo serum samples from untreated and treated mice, as well as from human donors.

The ELISAs were performed as described, diluting serum samples 100-fold, interpolating the serum human ANGPTL8 concentration by comparing the optical densities of the diluted samples to those of the monomer human ANGPTL8 protein (human ANGPTL8 dimer protein with mouse Fc tag) standard curve.

Figure 4:
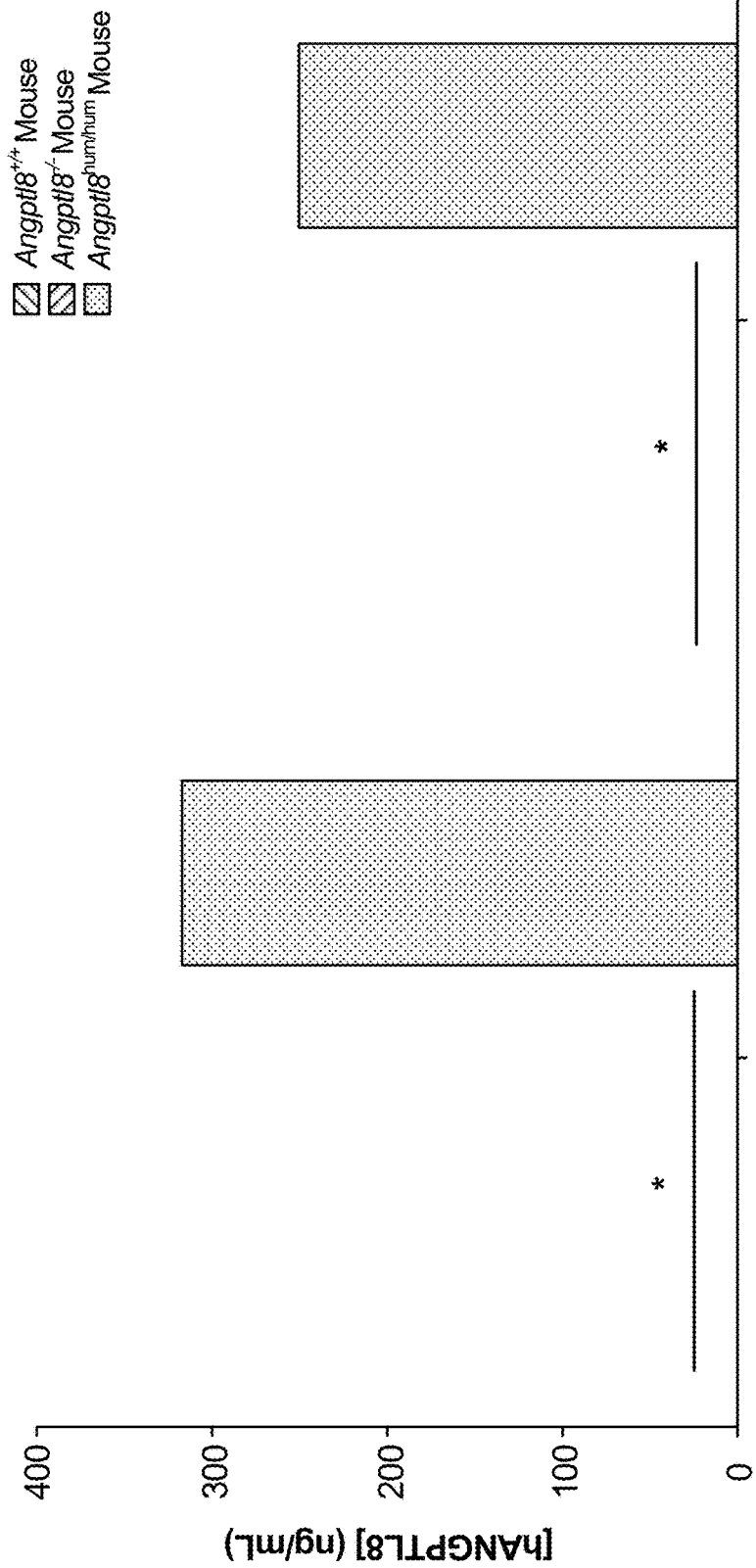
FIG. 4 shows, in bar graph form, the results of applying the ELISA system described herein to test serum samples from wild type, knockout, and ANGPTL8 humanized mice.

The selected Regeneron capture and detection mAbs show specificity for human ANGPTL8 and no cross-reactivity to mouse ANGPTL8 (FIG. 4).

Example 4: Testing of Various Human ANGPTL8 Proteins in a Standard Curve

H4H15347P was selected as capture, and biotin-H4H15318P as detection, mAbs for the further ELISA development. In order to quantify human ANGPTL8 levels in biological samples, it is critical for the ELISA to utilize a human ANGPTL8 protein as a standard to produce reliable optical densities from which to interpolate the concentrations of human ANGPTL8 in test samples. Ideally, there should be a sigmoidal, dose-response curve, with a wide linear range, with several quantified points within that range, and low background signal. The instant experiment compared several forms of human ANGPTL8 protein as a standard in the ELISA.

The following human ANGPTL8 protein forms were serially-diluted 2-fold in PBS, in a 12-point curve, from 50 ng/mL-0ng/mL: human ANGPTL8 dimer with mouse Fc tag (human ANGPTL8 monomer protein with myc-myc-his tag), human ANGPTL8 monomer with mouse myc-myc-his tag (human ANGPTL8 dimer protein with mouse Fc tag), untagged human ANGPTL8 protein in buffer containing detergent (outsourced production, Genscript), and untagged human ANGPTL8 protein in buffer without detergent (outsourced production, Genscript).

Figure 5:
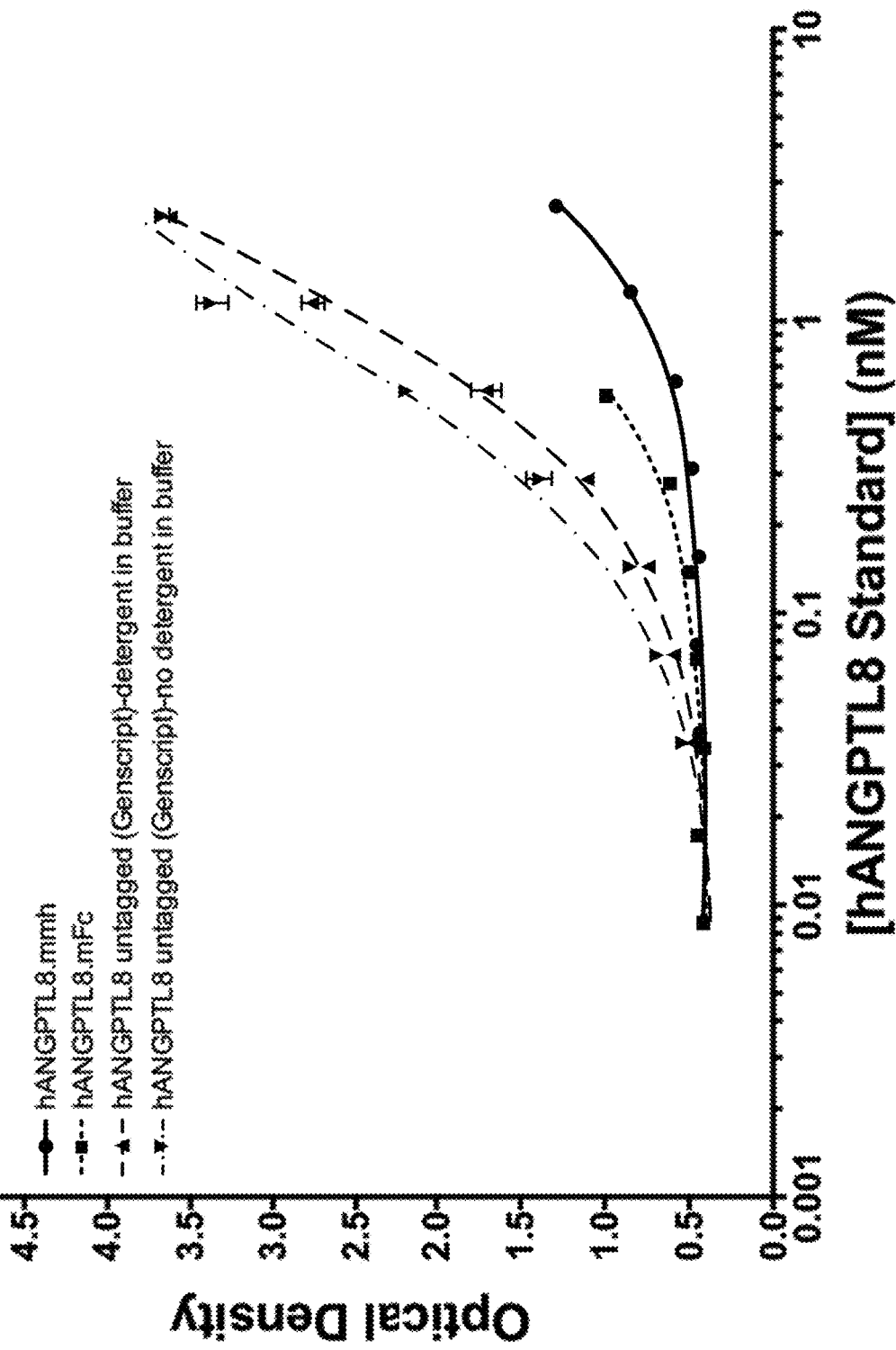
FIG. 5 graphically depicts the results of testing various forms of human ANGPTL8 proteins to use as the standard protein in the ELISA system described herein.

The two human ANGPTL8 untagged proteins from Genscript (in different buffers) produced the best dose-response standard curves (comparable to each other), with the lowest background signal, the widest linear range, and the most number of points along the curve (FIG. 5).

Example 5: Validation of Standard Curve Using Serum Spike-In

It is important that the ELISA platform can detect human ANGPTL8 in biological samples, and that the optical densities obtained are true read-outs of the target protein concentration, unaffected by the many cofactors that are endogenously present in serum and plasma.

The instant experiment serially-diluted the untagged human ANGPTL8 protein standard as previously described in PBS, and compared this standard curve to those obtained by diluting the standard protein in the same manner, but in 1% mouse Angptl8$^{-/-}$ serum matrix and in 1% human serum matrix.

Figure 6:
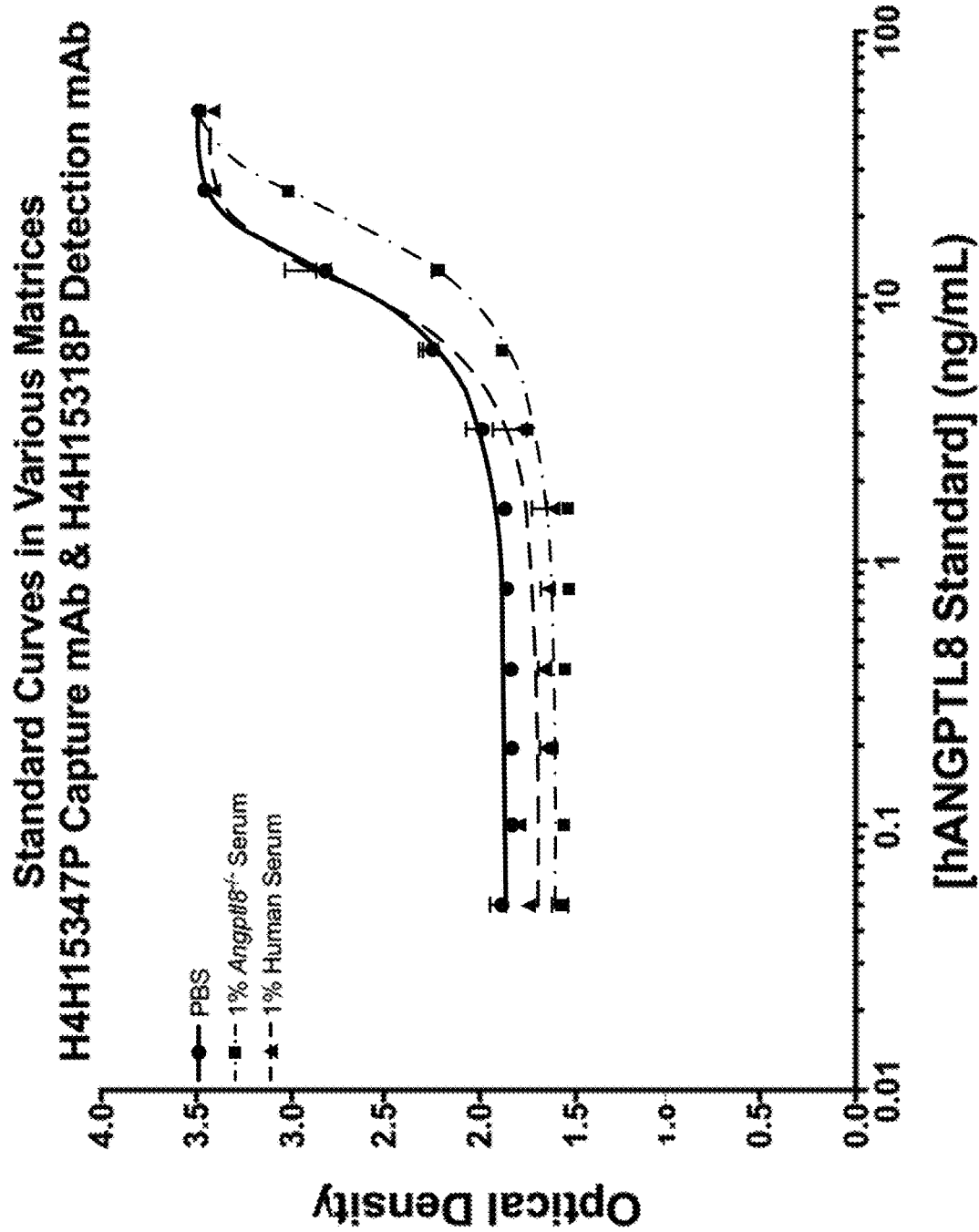
FIG. 6 graphically depicts the results of serially diluting human ANGPTL8 standard protein in various matrices to generate standard curves, in order to verify that the presence of serum cofactors do not impact the results of the ELISA system described herein.
Figure 8A:
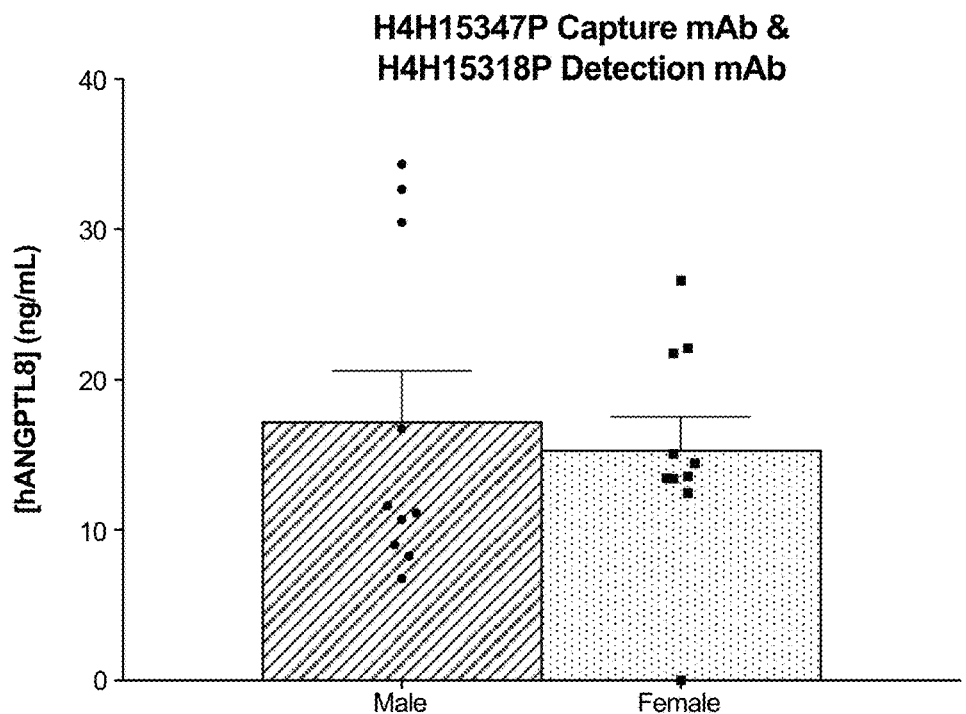
FIG. 8A shows, in bar graph form, the results of measuring the human ANGPTL8 protein concentrations in human male and female serum samples, based on diluting the serum 1:10 in PBS, and interpolating the raw optical densities from the standard curve, and accounting for the dilution factor.
Figure 8B:
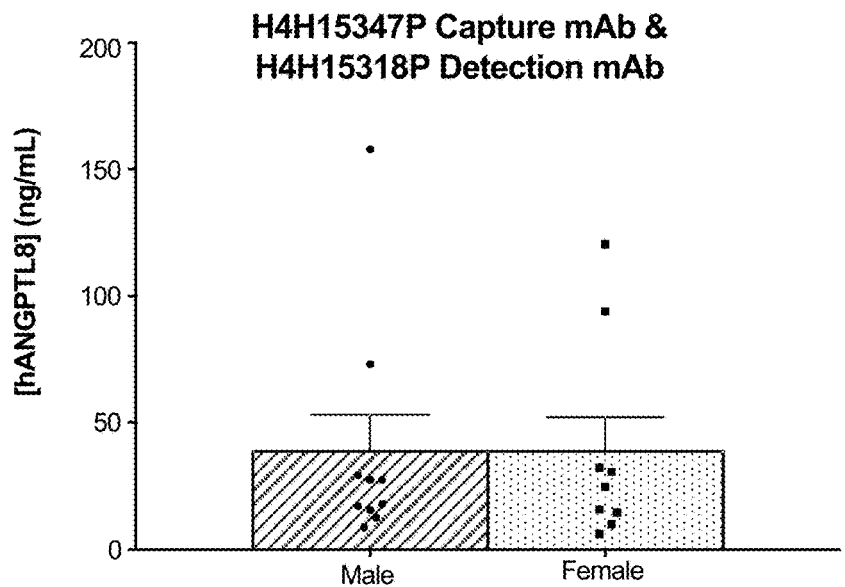
FIG. 8B shows, in bar graph form, the results of measuring the human ANGPTL8 protein concentrations in human male and female plasma samples, based on diluting the plasma 1:10 in PBS, and interpolating the raw optical densities from the standard curve, and accounting for the dilution factor.

The optical densities obtained in the standard curve are true measurements of human ANGPTL8 protein, and not influenced by the presence of endogenous serum cofactors (FIG. 6).

Example 6: Validation of Human ANGPTL8 ELISA Specificity

For this ELISA system to be a reliable method for human ANGPTL8 quantification, specificity for the human ANGPTL8 protein is key. While a previous ELISA experiment confirmed that the mAbs of this ELISA are specific for the human form of ANGPTL8, the instant experiment verifies that the mAbs are specific for human ANGPTL8, as opposed to similar proteins, human ANGPTL3 and human ANGPTL4, which are members of the same family of proteins. Furthermore, it has been established that ANGPTL3 and ANGPTL8 proteins interact with each other for biological effect. Therefore, it needs to be determined whether the ELISA system described herein is able to detect human ANGPTL8 in the presence of human ANGPTL3, and that human ANGPTL3 presence in no way affects the measurement of human ANGPTL8 protein levels.

Standard curves of the following human proteins were generated using 2-fold serial dilutions, 12 points, from 200 ng/mL-0ng/mL in PBS: ANGPTL8, ANGPTL3, ANGPTL4, and ANGPTL8 with spiked-in ANGPTL3. These curves were compared to one another.

The ELISA described herein is specific for the human ANGPTL8 protein, and does not detect human ANGPTL3 or human ANGPTL4. The presence of human ANGPTL3 with human ANGPTL8 does not affect the system's ability to detect human ANGPTL8 (FIG. 7).

Example 7. Measurement of Human ANGPTL8 Concentration in Human Serum and Plasma Samples Often, biological samples are too concentrated with proteins to run undiluted, or "neat," in a plate-based ELISA system; therefore, it is usually necessary to dilute the samples, so that the target protein can be properly detected, and its concentration can be measured. Troubleshooting with various dilutions of sample is typical in ELISA development, with the goal being the determination of a dilution factor that results in the optical densities of the samples falling within the linear range of the standard curve. Since the goal of the ELISA described herein is to reliably detect and quantify the concentration of human ANGPTL8 protein in human samples (serum and plasma), it is important to validate this system using serum and plasma samples collected from human donors. It is also necessary to optimize the ELISA described herein by determining a proper dilution factor of human serum and plasma samples so that, when applied as samples, the optical densities fall within the linear range of the human ANGPTL8 standard curve. This way, it can be certain that the interpolated values of the samples (taking into account the linear range of the standard curve, and the dilution factor of the samples) are reliable measurements of circulating human ANGPTL8 protein concentration.

Serum (collected without anti-coagulant) and plasma (collected with lithium heparin as anti-coagulant) samples were purchased from commercial vendor, Bioreclamation IVT, who obtained them from male and female human donors. Each of these samples were run in the ELISA as described, using H4H15347P as capture mAb, applying the following dilutions of each sample: 1:5, 1:10, and 1:50 in PBS. The optical densities of each sample, at each dilution, were examined, and compared to the standard curve, in order to determine which dilution factor results in optical densities lying within the linear range of the human ANGPTL8 protein standard curve.

Human ANGPTL8 was able to be detected in human male and female, serum (N=10/gender) and plasma (N=10/gender) samples. Using H4H15347P as the capture mAb in the ELISA, a dilution of 1:10 serum or plasma:PBS proved to be the optimal dilution. At the 1:10 dilution, the sample optical densities fell within the linear range of the standard curve, and the human ANGPTL8 protein concentrations were determined by interpolating the values from the standard curves and transforming the values according to the dilution factor of 10. Using H4H15347P as the capture mAb in the ELISA, the 1:5 dilution factor resulted in similar interpolated human ANGPTL8 protein concentrations in the samples, while the 1:50 dilution factor proved to be too dilute to obtain any data. Males and females showed similar mean human ANGPTL8 concentrations to each other, for both serum and plasma.

What is claimed is:

1. A method for detecting and/or quantifying human Angiopoietin-like protein 8 (hANGPTL8) in a sample, the method comprising:
   Obtaining a sample from a subject;
   Adding the sample to wells of an Enzyme Linked Immunosorbent Assay (ELISA) plate coated with a capture antibody, wherein the capture antibody is a first anti-hANGPTL8 antibody;
   Adding a detection antibody to the wells of the plate, wherein the detection antibody is a second anti-hANGPTL8 antibody bound to a tag;
   Adding an agent that binds the tag, wherein the agent is conjugated to an enzyme;
   Adding a substrate for the enzyme; and
   Measuring the amount of product of the enzyme-substrate reaction, wherein the capture antibody is H4H15347P or H4H15361P2, wherein H4H15347P comprises three heavy chain complementarity determining regions HCDR1, HDCR2, and HCDR3 and three light chain complementarity determining regions LCDR1, LCDR2, and LCDR3, wherein HCDR1 comprises the amino acid sequence of SEQ ID NO: 228, HCDR2 comprises the amino acid sequence of SEQ ID NO: 230, HCDR3 comprises the amino acid sequence of SEQ ID NO: 232, LCDR1 comprises the amino acid sequence of SEQ ID NO: 236, LCDR2 comprises the amino acid sequence of SEQ ID NO: 238, and LCDR3 comprises the amino acid sequence of SEQ ID NO: 240, wherein H4H15361P2 comprises three heavy chain complementarity determining regions HCDR1, HDCR2, and HCDR3 and three light chain complementarity determining regions LCDR1, LCDR2, and LCDR3, wherein HCDR1 comprises the amino acid sequence of SEQ ID NO: 292, HCDR2 comprises the amino acid sequence of SEQ ID NO: 294, HCDR3 comprises the amino acid sequence of SEQ ID NO: 296, LCDR1 comprises the amino acid sequence of SEQ ID NO: 252, LCDR2 comprises the amino acid sequence of SEQ ID NO: 254, and LCDR3 comprises the amino acid sequence of SEQ ID NO: 256.

2. The method of claim 1, wherein the detection antibody is H4H15318P, wherein H4H15318P comprises three heavy chain complementarity determining regions HCDR1, HDCR2, and HCDR3 and three light chain complementarity determining regions LCDR1, LCDR2, and LCDR3, wherein HCDR1 comprises the amino acid sequence of SEQ ID NO: 36, HCDR2 comprises the amino acid sequence of SEQ ID NO: 38, HCDR3 comprises the amino acid sequence of SEQ ID NO: 40, LCDR1 comprises the amino acid sequence of SEQ ID NO: 44, LCDR2 comprises the amino acid sequence of SEQ ID NO: 46, and LCDR3 comprises the amino acid sequence of SEQ ID NO: 48.

3. The method of claim 2, wherein the capture antibody is H4H15347P, and the detection antibody is H4H15318P.

4. The method of claim 1, wherein the tag is biotin.

5. The method of claim 1, wherein the agent is streptavidin.

6. The method of claim 1, wherein the enzyme is horseradish peroxidase (HRP).

7. The method of claim 1, wherein the substrate is a chromogenic substrate.

8. The method of claim 7, wherein the chromogenic substrate is 3,3',5,5'-tetramethylbenzidine (TMB).

9. The method of claim 1, wherein the method does not detect (and/or quantify) non-human ANGPTL8.

10. The method of claim 1, wherein the method does not detect (and/or quantify) hANGPTL3 nor hANGPTL4.

11. The method of claim 1, wherein the sample is plasma or serum.

12. The method of claim 11, wherein the serum or plasma is diluted 1:10 in PBS.

13. The method of claim 1, wherein the subject is human.

\* \* \* \* \*

SEQUENCE LISTING

<160> NUMBER OF SEQ ID NOS: 345

<210> SEQ ID NO 1
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtgcagtc tggggctgag gtgaagaagc ctggggcctc agtgaaggtc     60
tcctgcaagg cttctggata caccttcacc agttatgata tcaattgggt gcgacaggcc    120
actggacaag ggcttgagtg gatggggtgg atgaacccta acggtgataa cacaggctat    180
gcacagaagt tccagggcag agtcaccatg accgggaca cctccataag cacagcctac    240
atggagctga gcagcctgag atctgaggac acggccgtgt attactgtgc gagagaggga    300
atttgggggt tcgaccctg gggccaggga accctggtca ccgtctcctc a              351

<210> SEQ ID NO 2
<211> LENGTH: 117

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Gly Asp Asn Thr Gly Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Trp Gly Phe Asp Pro Trp Gly Gln Gly Thr Leu
            100                 105                 110

Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggatacacct tcaccagtta tgat                                          24

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Ser Tyr Asp
1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgaacccta acggtgataa caca                                          24

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 6

Met Asn Pro Asn Gly Asp Asn Thr
1               5

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgagagagg gaatttgggg gttcgacccc                                      30

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Glu Gly Ile Trp Gly Phe Asp Pro
1               5                   10

<210> SEQ ID NO 9
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gacatccaga tgacccagtc tccatcctcc ctgtctgcat ctgtaggaga cagagtcacc      60
atcacttgcc gggcaagtca ggacattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttttta ctgtctacag cataatactt ccctcggac gttcggccaa     300 gggaccaagg tggaaatcaa a                                              321

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Phe Tyr Cys Leu Gln His Asn Thr Phe Pro Arg
                85                  90                  95

Thr Phe Gly Gln Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caggacatta gaaatgat                                                 18

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Asp Ile Arg Asn Asp
1               5

<210> SEQ ID NO 13
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gctgcatcc                                                            9

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
ctacagcata atactttccc tcggacg                                        27

<210> SEQ ID NO 16

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Gln His Asn Thr Phe Pro Arg Thr
1               5

<210> SEQ ID NO 17
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gaagtgcagc tggtggagtc tgggggaggc ttggtacagc ctggcaggtc cctgagactc      60
tcctgtgcag cctctggatt catctttgat gattatgaca tgcactgggt ccggcaagct     120
ccagggaagg gcctggagtg gtctcaggt attagttgga atagtggtag taaaggctat      180
gcggactctg tgaagggccg attcaccatc tccagagaca cgccaagaa ctccctgtat      240 ctgcaaatga acagtctgag agctgaggac acggccttgt attactgtac aaaagggccc     300
tgggactact ttgactactg gggccaggga accctggtca ccgtctcctc a              351

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Ile Phe Asp Asp Tyr
            20                  25                  30

Asp Met His Trp Val Arg Gln Ala Pro Gly Lys Gly Leu Glu Trp Val
        35                  40                  45

Ser Gly Ile Ser Trp Asn Ser Gly Ser Lys Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Lys Gly Pro Trp Asp Tyr Phe Asp Tyr Trp Gly Gln Gly Thr Leu
            100                 105                 110

Val Thr Val Ser Ser
        115

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 19
ggattcatct ttgatgatta tgac                                              24

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Phe Ile Phe Asp Asp Tyr Asp
1               5

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
attagttgga atagtggtag taaa                                              24

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ser Trp Asn Ser Gly Ser Lys
1               5

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23 acaaagggc cctgggacta ctttgactac                                         30

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Thr Lys Gly Pro Trp Asp Tyr Phe Asp Tyr
1               5                   10

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
gacatccaga tgacccagtc tccttccacc ctgtctgcat ctgtaggaga cagagtcacc      60
atcacttgcc gggccagtca gagtattagt agctggttgg cctggtatca gcagaaacca    120
gggaaagccc ctaagctcct gatctataag gcgtctagtt tagaaaatgg ggtcccatca    180
aggttcagcg gcagtggatc tgggacagaa ttcactctca ccatcagcag cctgcagcct    240
gatgattttg caacttatta ctgccaacag tataatagtt attcgtacac ttttggccag    300
gggaccaagc tggagatcaa a                                               321
```

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

```
cagagtatta gtagctgg                                                    18
```

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Gln Ser Ile Ser Ser Trp
1               5
```

<210> SEQ ID NO 29
<211> LENGTH: 9
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 29 aaggcgtct                                                                         9

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Lys Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
caacagtata atagttattc gtacact                                                    27

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln Gln Tyr Asn Ser Tyr Ser Tyr Thr
1               5

<210> SEQ ID NO 33
<211> LENGTH: 378
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
caggtgcagc tggtggagtc tgggggaggc gtggtccagc ctggggaggtc cctgagactc                60 tcctgtacag cctccggatt caccttcgga aactttggca tacactgggt ccgccaggct               120
ccaggcaagg ggctggagtg ggtggcggtc atatcatatg atggaactga taaattctat               180
gcagaccccg tgaagggccg attcattatc tccagagaca attctatgaa cattctgtat               240
ctgcaaatga acagcctgag agctgaagac acggctgtat actattgtgc gaaagatggg               300
gaaatggaac tacggggata ctattactac tacggaatgg acgtctgggg ccaagggacc               360
acggtcaccg tctcctca                                                            378

<210> SEQ ID NO 34
<211> LENGTH: 126
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 34

```
Gln Val Gln Leu Val Glu Ser Gly Gly Gly Val Val Gln Pro Gly Arg
1               5                  10                  15

Ser Leu Arg Leu Ser Cys Thr Ala Ser Gly Phe Thr Phe Gly Asn Phe
            20                  25                  30

Gly Ile His Trp Val Arg Gln Ala Pro Gly Lys Gly Leu Glu Trp Val
        35                  40                  45

Ala Val Ile Ser Tyr Asp Gly Thr Asp Lys Phe Tyr Ala Asp Pro Val
    50                  55                  60

Lys Gly Arg Phe Ile Ile Ser Arg Asp Asn Ser Met Asn Ile Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Glu Met Glu Leu Arg Gly Tyr Tyr Tyr Tyr Tyr Gly
            100                 105                 110

Met Asp Val Trp Gly Gln Gly Thr Thr Val Thr Val Ser Ser
        115                 120                 125
```

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ggattcacct tcggaaactt tggc                                          24

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

```
Gly Phe Thr Phe Gly Asn Phe Gly
1               5
```

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
atatcatatg atggaactga taaa                                          24

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Ile Ser Tyr Asp Gly Thr Asp Lys
1               5

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcgaaagatg gggaaatgga actacgggga tactattact actacggaat ggacgtc        57

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Asp Gly Glu Met Glu Leu Arg Gly Tyr Tyr Tyr Tyr Tyr Gly
1               5                   10                  15

Met Asp Val

<210> SEQ ID NO 41
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gacatccaga tgacccagtc tccatcttcc gtgtctgcat ctgttggaga cagagtcacc       60
attacttgtc gggcgagtca gggtattaac acctggttag cctggtatca gcagaaacca      120
gggacagccc caaagctcct gatctttgct gcatccagtt tggagagcgg agtcccatca      180
aggttcagcg gcagtggatt tggtacagat tcactctca ccatcagcag cctacagtct       240
gaggatcttg caacttactt ttgtcaacag gttcacagtc ccccgtacac ttttggccag      300
gggaccaagc tggagatcaa a                                                 321

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Thr Trp
                20                  25                  30

Leu Ala Trp Tyr Gln Gln Lys Pro Gly Thr Ala Pro Lys Leu Leu Ile
            35                  40                  45

Phe Ala Ala Ser Ser Leu Glu Ser Gly Val Pro Ser Arg Phe Ser Gly

```
                50                  55                  60
Ser Gly Phe Gly Thr Asp Phe Thr Leu Thr Ile Ser Ser Leu Gln Ser
 65                  70                  75                  80

Glu Asp Leu Ala Thr Tyr Phe Cys Gln Gln Val His Ser Pro Pro Tyr
                 85                  90                  95

Thr Phe Gly Gln Gly Thr Lys Leu Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cagggtatta acacctgg                                                  18

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Asn Thr Trp
 1               5

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 gctgcatcc                                                             9

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caacaggttc acagtccccc gtacact                                        27

```
<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Val His Ser Pro Pro Tyr Thr
1               5

<210> SEQ ID NO 49
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gaggtgcagc tggtggagtc tggaggaggt gtggtacggc cggggggtc actgagactc        60 tcctgtgctg cctctggatt caccgttgat gattatgaca tgagttgggt ccgccaaact      120
ccaggaaagg gctggagtg gatctctggc attaattgga atggaggtaa cacaggttat      180
gcagactctg tgaagggccg attcatcatc tccagagaca gcgccaagaa ctccctgttt      240
ctgcaaatga acagtctgag agccgaggac acggccttgt atcactgttg gggagcgatt      300
ggtgcttttg atatttgggg ccaagggaca atggtcaccg tctcttca                 348

<210> SEQ ID NO 50
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Val Asp Asp Tyr
            20                  25                  30

Asp Met Ser Trp Val Arg Gln Thr Pro Gly Lys Gly Leu Glu Trp Ile
        35                  40                  45

Ser Gly Ile Asn Trp Asn Gly Gly Asn Thr Gly Tyr Ala Asp Ser Val
    50                  55                  60

Lys Gly Arg Phe Ile Ile Ser Arg Asp Ser Ala Lys Asn Ser Leu Phe
65                  70                  75                  80

Leu Gln Met Asn Ser Leu Arg Ala Glu Asp Thr Ala Leu Tyr His Cys
                85                  90                  95

Trp Gly Ala Ile Gly Ala Phe Asp Ile Trp Gly Gln Gly Thr Met Val
            100                 105                 110

Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 51
ggattcaccg ttgatgatta tgac                                              24

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Phe Thr Val Asp Asp Tyr Asp
1               5

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
attaattgga atggaggtaa caca                                              24

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Asn Trp Asn Gly Gly Asn Thr
1               5

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
tggggagcga ttggtgcttt tgatatt                                           27

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gly Ala Ile Gly Ala Phe Asp Ile
1               5

<210> SEQ ID NO 57
<211> LENGTH: 336
<212> TYPE: DNA
<213> ORGANISM: Artificial Sequence
<220> FEATURE:

<223> OTHER INFORMATION: Description of Artificial Sequence: Synthetic
     polynucleotide

<400> SEQUENCE: 57

```
gatattgtga tgacccagtc tccactctcc tcacctgtca cccttggaca gccggcctcc    60
atctcctgca ggtctagtca aagcctcgta cacagtgatg gcggcaccta cttgagttgg   120
cttcagcaga ggccaggcca gcctccaaga ctcctaattt ataagatttt taaccggttc   180
tctggggtcc cagacagatt cagtggcagt ggggcaggga cagatttcac actgagaatc   240
agtagggtgg aagctgagga tgtcgggggtt tattactgca tgcaaacaac acaatttccg   300
ctcactttcg gcggagggac caaggtggag atcaaa                              336
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 58

Asp Ile Val Met Thr Gln Ser Pro Leu Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Gly Thr Tyr Leu Ser Trp Leu Gln Gln Arg Pro Gly Gln Pro
        35                  40                  45

Pro Arg Leu Leu Ile Tyr Lys Ile Phe Asn Arg Phe Ser Gly Val Pro
    50                  55                  60

Asp Arg Phe Ser Gly Ser Gly Ala Gly Thr Asp Phe Thr Leu Arg Ile
65                  70                  75                  80

Ser Arg Val Glu Ala Glu Asp Val Gly Val Tyr Tyr Cys Met Gln Thr
                85                  90                  95

Thr Gln Phe Pro Leu Thr Phe Gly Gly Gly Thr Lys Val Glu Ile Lys
            100                 105                 110

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 59

```
caaagcctcg tacacagtga tggcggcacc tac                                  33
```

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 60

Gln Ser Leu Val His Ser Asp Gly Gly Thr Tyr
1               5                   10

<210> SEQ ID NO 61
<211> LENGTH: 9

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 aagattttt                                                                9

<210> SEQ ID NO 62
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Ile Phe
1

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
atgcaaacaa cacaatttcc gctcact                                           27

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Gln Thr Thr Gln Phe Pro Leu Thr
1               5

<210> SEQ ID NO 65
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gaggtgcagc tggtggagtc tgggggaggc ttggtacagc ctggggggtc cctgagactc       60
tcctgtgcag cctctggatt caccttagc agctatgcca tgagctgggt ccgccaggct       120
ccagggaagg ggctggagtg ggtctcagct attactggta gtggtggtag aacatactac      180
gcagactccg tgaagggccg gttcaccatc tccagagaca atgccaagaa cacgctgtat      240
ctgcaaatga acagcctgag agccgaggac acggccgtat attactgtgc gaaaaacttt     300 cccttttgact actggggcca gggaaccctg gtcaccgtct cctca                    345

<210> SEQ ID NO 66
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Thr Gly Ser Gly Gly Arg Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Phe Pro Phe Asp Tyr Trp Gly Gln Gly Thr Leu Val Thr
            100                 105                 110

Val Ser Ser
        115
```

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggattcacct ttagcagcta tgcc                                          24

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Gly Phe Thr Phe Ser Ser Tyr Ala
1               5
```

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
attactggta gtggtggtag aaca                                          24

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Thr Gly Ser Gly Gly Arg Thr
1               5

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcgaaaaact ttccctttga ctac                                          24

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Lys Asn Phe Pro Phe Asp Tyr
1               5

<210> SEQ ID NO 73
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gacatcgtga tgacccagtc tccagactcc ctggctgtgt ctctgggcga gagggccacc     60
atcaactgcg agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagattt cactctcacc    240
atcagcaccc tgcaggctga ggatgtggca gtttattact gtcagcaata ttatagtact    300
ccgtacactt ttggccaggg gaccaagctg gagatcaaa                           339

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr 65                  70                  75                  80
Ile Ser Thr Leu Gln Ala Glu Asp Val Ala Val Tyr Tyr Cys Gln Gln
                    85                  90                  95

Tyr Tyr Ser Thr Pro Tyr Thr Phe Gly Gln Gly Thr Lys Leu Glu Ile
            100                 105                 110

Lys

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagagtgttt tatacagctc caacaataag aactac                                    36

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ser Val Leu Tyr Ser Ser Asn Asn Lys Asn Tyr
1               5                   10

<210> SEQ ID NO 77
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77 tgggcatct                                                                   9

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Trp Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
cagcaatatt atagtactcc gtacact                                              27

<210> SEQ ID NO 80

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Tyr Tyr Ser Thr Pro Tyr Thr
1               5

<210> SEQ ID NO 81
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
gaggtgcagc tggtggagtc tgggggaggc ttggtacagc ctggggggtc cctgagactc      60
tcctgtgcag cctctggatt caccttttcc agctatgcca tgacctgggt ccgccaggct     120
ccagggaagg gctggagtg gtctcagct attagtggta gtggtggtag cacatactac     180
acagactccg tgaagggccg gttcaccctc tccagagaca attccaagaa cacgctgtat     240
ctgcaaatga acagcctgag agccgaggac acggccgtat attactgtgc gaaatctgac     300
tacagtaaca ccatctactg gtactacggt atggacgtct ggggccaagg gaccacggtc     360
accgtctcct ca                                                         372

<210> SEQ ID NO 82
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Thr Tyr Tyr Thr Asp Ser Val
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Asp Tyr Ser Asn Thr Ile Tyr Trp Tyr Tyr Gly Met Asp
            100                 105                 110

Val Trp Gly Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic -continued

```
        oligonucleotide

<400> SEQUENCE: 83
ggattcacct tttccagcta tgcc                                           24

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Thr Phe Ser Ser Tyr Ala
1               5

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
attagtggta gtggtggtag caca                                           24

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Ser Gly Ser Gly Gly Ser Thr
1               5

<210> SEQ ID NO 87
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcgaaatctg actacagtaa caccatctac tggtactacg gtatggacgt c             51

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Lys Ser Asp Tyr Ser Asn Thr Ile Tyr Trp Tyr Tyr Gly Met Asp
1               5                   10                  15

Val

<210> SEQ ID NO 89
<211> LENGTH: 321
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtgggtc tgggacagat ttcactctca ccatcagcag tctgcaacct   240
gaagattttg caacttacta ctgtcaacag agttacagta ccccctcggac gttcggccaa   300 gggaccaagg tggaaatcaa a                                             321

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cagagcatta gcagctat                                                  18

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Ser Ile Ser Ser Tyr
1               5
```

<210> SEQ ID NO 93
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 gctgcatcc                                                                  9

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
caacagagtt acagtacccc tcggacg                                             27

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Ser Tyr Ser Thr Pro Arg Thr
1               5

<210> SEQ ID NO 97
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
caggtgcagc tggtggagtc tgggggaggc ttggtcaagc ctggagggtc cctgagactc          60
tcctgtgcag cctctggatt caccttcagt gactactata tgagctggat ccgccaggct         120
ccagggaagg gactggagtg gatttcacac attagtggta gtggtagaac cacacactac         180
gcagactcta tgaagggccg attcaccatt tccagggaca cgccaagaa ctcactgtat          240 ttgcaaatga acagcctgag agccgaggac acggccgtgt attactgtgt gagagaggga         300
ggttttaact ggaactacga gggtactttt gatatctggg gccagggac aatggtcacc          360 gtctcttca                                                                369

<210> SEQ ID NO 98
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser His Ile Ser Gly Ser Gly Arg Thr Thr His Tyr Ala Asp Ser Met
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Gly Gly Phe Asn Trp Asn Tyr Glu Gly Thr Phe Asp Ile
            100                 105                 110

Trp Gly Gln Gly Thr Met Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggattcacct tcagtgacta ctat                                          24

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Phe Thr Phe Ser Asp Tyr Tyr
1               5

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
attagtggta gtggtagaac caca                                          24

<210> SEQ ID NO 102
<211> LENGTH: 8
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 102

Ile Ser Gly Ser Gly Arg Thr Thr
1               5

<210> SEQ ID NO 103
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtgagagagg gaggttttaa ctggaactac gagggtactt ttgatatc                48

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Val Arg Glu Gly Gly Phe Asn Trp Asn Tyr Glu Gly Thr Phe Asp Ile
1               5                   10                  15

<210> SEQ ID NO 105
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gatattgtga tgacccagac tccactctct tcacctgtca cccttggaca gccggcctcc     60
atctcctgca ggtctagtca agcctcttta cacagtgatc aaaacaccta cttgagttgg    120
cttcaccaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcgggatt tattactgca tgcaaggtac acaatttccg    300
ctcactttcg gcggagggac caaggtggag atcaaa                              336

<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Leu His Ser
                20                  25                  30

Asp Gln Asn Thr Tyr Leu Ser Trp Leu His Gln Arg Pro Gly Gln Pro
            35                  40                  45

```
Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Ile Tyr Tyr Cys Met Gln Gly
                 85                  90                  95

Thr Gln Phe Pro Leu Thr Phe Gly Gly Gly Thr Lys Val Glu Ile Lys
            100                 105                 110
```

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
caaagcctct tacacagtga tcaaaacacc tac                              33

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Gln Ser Leu Leu His Ser Asp Gln Asn Thr Tyr
 1               5                  10
```

<210> SEQ ID NO 109
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 aagatttct                                                          9

<210> SEQ ID NO 110
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Lys Ile Ser
 1
```

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atgcaaggta cacaatttcc gctcact                                     27

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Gln Gly Thr Gln Phe Pro Leu Thr
1               5

<210> SEQ ID NO 113
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gaggtgcagc tggtggagtc tgggggagg cttggtacag ggggggggtc cctgagactc        60
tcctgtgaag cctctggatt cacatttagc agctttgcca tgaactgggt ccgccaggct      120
ccagggaagg gctggagtg gtctcaggt cttagtggta gtggtagaag tacatactac        180
gcagactccg tgaagggccg gttcaccatc tccagagaca actccaagaa tagactctat     240
ttgcaaatgg acagcctgag agccgaggac tcggccgtat attattgtgc ggcctacgtg     300
ttacgaattt tggatcggtg gttcgacccc tggggccagg gaaccctggt caccgtctcc     360
tca                                                                    363

<210> SEQ ID NO 114
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Arg Leu Gly Thr Gly Gly Gly
1               5                   10                  15

Ser Leu Arg Leu Ser Cys Glu Ala Ser Gly Phe Thr Phe Ser Ser Phe
                20                  25                  30

Ala Met Asn Trp Val Arg Gln Ala Pro Gly Lys Gly Leu Glu Trp Val
            35                  40                  45

Ser Gly Leu Ser Gly Ser Gly Arg Ser Thr Tyr Tyr Ala Asp Ser Val
        50                  55                  60

Lys Gly Arg Phe Thr Ile Ser Arg Asp Asn Ser Lys Asn Arg Leu Tyr
65                  70                  75                  80

Leu Gln Met Asp Ser Leu Arg Ala Glu Asp Ser Ala Val Tyr Tyr Cys
                85                  90                  95

Ala Ala Tyr Val Leu Arg Ile Leu Asp Arg Trp Phe Asp Pro Trp Gly
                100                 105                 110

Gln Gly Thr Leu Val Thr Val Ser Ser
            115                 120

<210> SEQ ID NO 115
<211> LENGTH: 24
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 115
ggattcacat ttagcagctt tgcc                                              24

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Thr Phe Ser Ser Phe Ala
1               5

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cttagtggta gtggtagaag taca                                              24

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Ser Gly Ser Gly Arg Ser Thr
1               5

<210> SEQ ID NO 119
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcggcctacg tgttacgaat tttggatcgg tggttcgacc cc                           42

<210> SEQ ID NO 120
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ala Tyr Val Leu Arg Ile Leu Asp Arg Trp Phe Asp Pro
1               5                   10

<210> SEQ ID NO 121

<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gatattgtga tgactcagtc tccactctcc ctgcccgtca cccctggaga gccggcctcc    60
atctcctgca ggtctagtca gagcctcctt cataggactg gatacaacta tttggactgg   120
tacctgcaga agccagggca gtctccacag atcctgatct atttgggttc ttatcgggcc   180
tccggggtcc ctgacaggtt cagtggcagt ggatcaggca cagattttac actgaagatc   240
agcagagtgg aggctgaaga tgttggggtt tattactgca tgcaagctct acaaactccg   300
tggacgttcg gccaagggac caaggtggaa atcaaa                             336

<210> SEQ ID NO 122
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
            20                  25                  30

Thr Gly Tyr Asn Tyr Leu Asp Trp Tyr Leu Gln Lys Pro Gly Gln Ser
        35                  40                  45

Pro Gln Ile Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 123
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagagcctcc ttcataggac tggatacaac tat                                 33

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Ser Leu Leu His Arg Thr Gly Tyr Asn Tyr
1               5                   10

<210> SEQ ID NO 125
<211> LENGTH: 9
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 125 ttgggttct                                                                  9

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 126

Leu Gly Ser
1

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 127
atgcaagctc tacaaactcc gtggacg                                             27

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 128

Met Gln Ala Leu Gln Thr Pro Trp Thr
1               5

<210> SEQ ID NO 129
<211> LENGTH: 354
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 129
caggtgcagc tgcaggagtc gggcccagga ctggtgaagc cttcacagac cctgtccctc         60
acctgcactg tctctggtgg ctccatcaac agtggtggtt actactggaa ctggatccgc        120
cagcacccag gaagggcct ggagtggatt gggtacatct attacagtgg gagcacctac         180
ttcaacccgt ccctcaagag tcgagttacc atatcaatag acacgtctaa gaaccagttc        240
tccctgaagc tgagctctgt gactgccgcg gacacggccg tgtattactg tgcgagagag        300
gggatttatg cttttgacta ctggggccag ggaaccctgg tcaccgtctc ctca             354

```
<210> SEQ ID NO 130
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Phe Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ile Tyr Ala Phe Asp Tyr Trp Gly Gln Gly Thr
            100                 105                 110

Leu Val Thr Val Ser Ser
        115

<210> SEQ ID NO 131
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggtggctcca tcaacagtgg tggttactac                                          30

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gly Ser Ile Asn Ser Gly Gly Tyr Tyr
1               5                   10

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
atctattaca gtgggagcac c                                                   21

<210> SEQ ID NO 134
<211> LENGTH: 7
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 134

Ile Tyr Tyr Ser Gly Ser Thr
1               5

<210> SEQ ID NO 135
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcgagagagg ggatttatgc ttttgactac                                      30

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Arg Glu Gly Ile Tyr Ala Phe Asp Tyr
1               5                   10

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctattct gcatccagtt tgcaaagtgg ggtcccatca     180
aggttcggcg gcagtggatc tgggacagaa ttcactctca caatcagcag cctgcagcct     240
gaagattttg caacttatta ctgtctacaa cataatagtt acccgtggac gttcggccaa     300
gggaccaagg tggaaatcaa a                                              321

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

```
Tyr Ser Ala Ser Ser Leu Gln Ser Gly Val Pro Ser Arg Phe Gly Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
cagggcatta gaaatgat                                                 18

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gln Gly Ile Arg Asn Asp
 1               5
```

<210> SEQ ID NO 141
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 tctgcatcc                                                            9

<210> SEQ ID NO 142
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Ser Ala Ser
 1
```

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ctacaacata atagttaccc gtggacg                                       27

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Leu Gln His Asn Ser Tyr Pro Trp Thr
1               5

<210> SEQ ID NO 145
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
caggtgcagc tggtggagtc tgggggaggc gtggtccagc ctggagggtc cctgagactc      60
tcctgtgcag cctctggatt caccttcaat aactatggca tacactgggt ccgccaggct     120
ccaggcaagg ggctggagtg ggtggcagtt atatcatatg atgaaagtaa taaatactat     180
gcagactccg tgaagggccg attcaccatc tccagagaca attccaagaa cacgctgtat     240
ctgcaaatga acagcctgag agctgaggac acggctgttt attactgtgc gaaagacata     300
cggatagcag ctcgtcggca ctactactac tacggtatgg acgtctgggg ccaagggacc     360
acggtcaccg tctcctca                                                  378

<210> SEQ ID NO 146
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Ile His Trp Val Arg Gln Ala Pro Gly Lys Gly Leu Glu Trp Val
        35                  40                  45

Ala Val Ile Ser Tyr Asp Glu Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Arg Ile Ala Ala Arg Arg His Tyr Tyr Tyr Tyr Gly
            100                 105                 110

Met Asp Val Trp Gly Gln Gly Thr Thr Val Thr Val Ser Ser
        115                 120                 125

<210> SEQ ID NO 147
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 147
ggattcacct tcaataacta tggc                                             24

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Phe Thr Phe Asn Asn Tyr Gly
1               5

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
atatcatatg atgaaagtaa taaa                                             24

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Ser Tyr Asp Glu Ser Asn Lys
1               5

<210> SEQ ID NO 151
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcgaaagaca tacggatagc agctcgtcgg cactactact actacggtat ggacgtc        57

<210> SEQ ID NO 152
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Lys Asp Ile Arg Ile Ala Ala Arg Arg His Tyr Tyr Tyr Tyr Gly
1               5                   10                  15
Met Asp Val
```

```
<210> SEQ ID NO 153
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gacatccaga tgacccagtc tccatcttcc gtgtctgcat ctgtaggaga cagagtcacc     60
atcacttgtc gggcgagtca gggtattagc aggtggttag cctggtatca gcagaaacca    120
gggaaagccc caaagctcct gatctatgct gcatccagtt tggaaagtgg ggtcccagca    180
aggttcagcg gcagtggatc tgggacagat ttcactctca ccatcagcag cctgcagcct    240
gaagattttg caacttacta ttgtcaacag gctaacagtt tcccaatcac tttcggccct    300
gggaccaaag tggatatcaa a                                              321

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Pro Gly Thr Lys Val Asp Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cagggtatta gcaggtgg                                                   18

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Gly Ile Ser Arg Trp
```

<210> SEQ ID NO 157
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157 gctgcatcc                                                                  9

<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ala Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
caacaggcta acagtttccc aatcact                                             27

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Gln Ala Asn Ser Phe Pro Ile Thr
1               5

<210> SEQ ID NO 161
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gaggtgcagc tggtggagtc tgggggaggc ttggtacagc ctggagggtc cctgagactc         60
tcctgtgcag cctctggatt caccttcaat aatcatgaaa tgaattgggt ccgccaggct        120
ccagggaagg gtctggagtg ggtttcatac attagtagta gtggtaatac cgtaacctac        180
gcagactttc tgaagggccg attcaccatc tccagagaca acgccaagaa ctcgctgttt        240
ctgcaaatga acagcctgcg agacgaggac acggctgttt attactgtgc gcagatcat         300 ttaagtggaa cctcccacac ttcttattgg ggccagggaa ccctggtcac cgtctcctca        360

<210> SEQ ID NO 162
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn His
            20                  25                  30

Glu Met Asn Trp Val Arg Gln Ala Pro Gly Lys Gly Leu Glu Trp Val
        35                  40                  45

Ser Tyr Ile Ser Ser Ser Gly Asn Thr Val Thr Tyr Ala Asp Phe Leu
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95

Ala Arg Asp His Leu Ser Gly Thr Ser Pro Leu Ser Tyr Trp Gly Gln
            100                 105                 110

Gly Thr Leu Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ggattcacct tcaataatca tgaa                                              24

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Phe Thr Phe Asn Asn His Glu
1               5

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
attagtagta gtggtaatac cgta                                              24

<210> SEQ ID NO 166
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 166

Ile Ser Ser Ser Gly Asn Thr Val
1               5

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcgcgagatc atttaagtgg aacctcccca ctttcttat                              39

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Arg Asp His Leu Ser Gly Thr Ser Pro Leu Ser Tyr
1               5                   10

<210> SEQ ID NO 169
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gacatccaga tgacccagtc tccatcctcc ctgtctgcat ctgtgggaga cagagtcacc        60
atcacttgcc aggcgagtca ggacattaac aactacttaa attggtttca gcagaaacca       120
gggaaagccc ctaaactcct gatcttcgat gcatccaatt tagaaacagg ggtcccatca       180
aggttcagtg gaagtggatc tgggacagat tttactttca ccatcagcag cctgcagcct       240
gaagatattg caacatattt ctgtcaacag tatgaaaatc tcccttacac ttttggccag       300
gggaccaagc tggagatcaa a                                                 321

<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Phe Gln Gln Lys Pro Gly Lys Ala Pro Lys Leu Leu Ile
        35                  40                  45
```

```
Phe Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Phe Cys Gln Gln Tyr Glu Asn Leu Pro Tyr
                85                  90                  95
Thr Phe Gly Gln Gly Thr Lys Leu Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
caggacatta acaactac                                              18

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

```
Gln Asp Ile Asn Asn Tyr
1               5
```

<210> SEQ ID NO 173
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173 gatgcatcc                                                         9

<210> SEQ ID NO 174
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

```
Asp Ala Ser
1
```

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
caacagtatg aaaatctccc ttacact                                    27

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gln Gln Tyr Glu Asn Leu Pro Tyr Thr
1               5

<210> SEQ ID NO 177
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
caggtgcagc tggtggagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtggcagtt atatcatatg ctggaagtaa taaatactat     180
gcagactccg tgaagggccg attcaccatc tccagagaca attccaagaa cacgctgtat     240
ctgcaaatga acggcctgag agctgaggac acggctgtgt attactgtgc gaaagatccc     300
tacggtgact acgaggggt tcttgactac tggggccagg gaaccctggt caccgtctcc     360
tca                                                                    363

<210> SEQ ID NO 178
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Ala Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Val Tyr Tyr Cys
                85                  90                  95

Ala Lys Asp Pro Tyr Gly Asp Tyr Glu Gly Val Leu Asp Tyr Trp Gly
            100                 105                 110

Gln Gly Thr Leu Val Thr Val Ser Ser
        115                 120

<210> SEQ ID NO 179
<211> LENGTH: 24
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 179
ggattcacct tcagtagcta tggc                                              24

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Phe Thr Phe Ser Ser Tyr Gly
1               5

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
atatcatatg ctggaagtaa taaa                                              24

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ile Ser Tyr Ala Gly Ser Asn Lys
1               5

<210> SEQ ID NO 183
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcgaaagatc cctacggtga ctacgagggg gttcttgact ac                          42

<210> SEQ ID NO 184
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Lys Asp Pro Tyr Gly Asp Tyr Glu Gly Val Leu Asp Tyr
1               5                   10

<210> SEQ ID NO 185
```

<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 185
gacatccaga tgacccagtc tccatcctcc ctgtctgcat ctgtaggaga cagagtcacc      60
atcacttgcc aggcgagtca ggacattagc aactatttaa attggtatca gcagaaacca    120
gggaaagccc ctaagctcct gatctacgat gcttccaatt tggaaacagg ggtcccatca    180
aggttcagtg aagtggatc tgggacagat tttactttca ccatcagcag cctgcagcct     240
gaagatattg caacatatta ctgtcagcag tatgatcatc tcccgatcac cttcggccaa    300
gggacacgac tggagattaa a                                              321

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp His Leu Pro Ile
                85                  90                  95

Thr Phe Gly Gln Gly Thr Arg Leu Glu Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
caggacatta gcaactat                                                   18

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Asp Ile Ser Asn Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189 gatgcttcc                                                                  9

<210> SEQ ID NO 190
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Asp Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cagcagtatg atcatctccc gatcacc                                             27

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Gln Tyr Asp His Leu Pro Ile Thr
1               5

<210> SEQ ID NO 193
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193
gaggtgcagc tggtggagtc tgggggaggc ttggttcagc ctggggggtc cctgagactc          60
tcctgtgcag cctctggatt cacctttagc acctatgcca tgagctgggt ccgccaggct         120
ccagggaagg ggctgagtg gtctcagtt attagtggta gttttattag cacatactac          180
gcagactccg tgaagggccg gttcaccatc tccagagaca attccaagaa cacgctgtat         240
ctgcaaatga ccagcctgag agccgaggac acggccgtat attactgtgc gaaaaactcc         300
ccctttgact actgggggcca gggaaccctg gtcaccgtct cctca                        345

<210> SEQ ID NO 194
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Val Ile Ser Gly Ser Phe Ile Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Ala Glu Asp Thr Ala Val Tyr Tyr Cys
                85                  90                  95

Ala Lys Asn Ser Pro Phe Asp Tyr Trp Gly Gln Gly Thr Leu Val Thr
            100                 105                 110

Val Ser Ser
        115

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 195
ggattcacct ttagcaccta tgcc                                          24

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Gly Phe Thr Phe Ser Thr Tyr Ala
1               5

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 197
attagtggta gttttattag caca                                          24

<210> SEQ ID NO 198
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 198

Ile Ser Gly Ser Phe Ile Ser Thr
1               5

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
gcgaaaaact cccctttga ctac                                          24

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Lys Asn Ser Pro Phe Asp Tyr
1               5

<210> SEQ ID NO 201
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
gacatcgtga tgacccagtc tccagactcc ctgactgtat ctctgggcga gagggccacc    60
atcaactgca agtccagcca gagtgtttta tacagctcca acaataagaa ctacttagct   120
tggtaccagc agaaaccagg acagcctcct aacctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatactact   300
ccgtggacgt tcggccgagg gaccaaggtg gagatcaaa                           339

<210> SEQ ID NO 202
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Ile Val Met Thr Gln Ser Pro Asp Ser Leu Thr Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45
```

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Trp Thr Phe Gly Arg Gly Thr Lys Val Glu Ile
                100                 105                 110

Lys

<210> SEQ ID NO 203
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
cagagtgttt tatacagctc caacaataag aactac                              36

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Ser Val Leu Tyr Ser Ser Asn Asn Lys Asn Tyr
1               5                   10

<210> SEQ ID NO 205
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205 tgggcatct                                                            9

<210> SEQ ID NO 206
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Trp Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207

-continued

```
cagcaatatt atactactcc gtggacg                                              27
```

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gln Gln Tyr Tyr Thr Thr Pro Trp Thr
1               5

<210> SEQ ID NO 209
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 209

```
gaggtgcagc tggtggagtc tgggggaggc ttggtacagc cggggggtc cctgagactc      60 tcctgtgcag cctctggatt cacctttagc aactatgcca tgagctgggt ccgccaggct    120
ccagggaagg gactggagtg ggtctcaact attagtgata ctggtggtag cacatactac    180
gcagactccg tgaagggccg gttcgccctc tccagagaca attccaggaa cacgctgtat    240
ctacaaatga acagcctgag agccgaggac acggccgtat attactgtgc gaaagagggg    300 ccccggact actggggaca gggcaccctg gtcaccgtct cctca                     345
```

<210> SEQ ID NO 210
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Asp Thr Gly Gly Ser Thr Tyr Tyr Ala Asp Ser Val
    50                  55                  60

Lys Gly Arg Phe Ala Leu Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Pro Pro Asp Tyr Trp Gly Gln Gly Thr Leu Val Thr
            100                 105                 110

Val Ser Ser
        115

<210> SEQ ID NO 211
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 211
ggattcacct ttagcaacta tgcc                                              24

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Phe Thr Phe Ser Asn Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
attagtgata ctggtggtag caca                                              24

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ile Ser Asp Thr Gly Gly Ser Thr
1               5

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
gcgaaagagg ggcccccgga ctac                                              24

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Lys Glu Gly Pro Pro Asp Tyr
1               5

<210> SEQ ID NO 217
<211> LENGTH: 321
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 217
gaaattgtgt tgacacagtc tccagccacc ctgtctttgt ctccagggga aagagccacc      60
ctctcctgca ggaccagtca gagtgtcagc atctacttag cctggtacca acagaaacct     120
ggccaggctc ccaggctcct catctatgat gcatccaaga gggccactgg catcccagcc     180
aggttcagtg gcagagggtc tgggacagac ttcactctca ccatcagcag cctagagcct     240
gaagattttg cagtttatta ctgtcagcag cgtagcaact ggcctctcac cttcggccaa     300
gggacacgac tggagattaa a                                                321

<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Val Ser Ile Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Arg Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Arg Leu Glu Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
cagagtgtca gcatctac                                                    18

<210> SEQ ID NO 220
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gln Ser Val Ser Ile Tyr
1               5

<210> SEQ ID NO 221
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 221 gatgcatcc					9

<210> SEQ ID NO 222
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Asp Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 223
cagcagcgta gcaactggcc tctcacc					27

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Gln Gln Arg Ser Asn Trp Pro Leu Thr
1               5

<210> SEQ ID NO 225
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 225
gaggtgcagc tggtggagtc tgggggaggc ttggtgcagc cggggggggtc cctgagactc					60
tcctgtgcag cctctggatt caccttcaga aactatgcca tgaactgggc ccgccaggct					120
ccagggaagg gactggagtg ggtctcaggt attactggta gtggtggtgc cacatactac					180
gcagactccg tgaagggccg gttcaccatc tccagagaaa attccaagaa cacgctgttt					240
ctgcaaatgg acaccctgag agccgaggac acggccgttt attattgtgc gaaagatcgg					300
aggtatttcc ctacttcggg gggtcctcag tggggccagg gaaccctggt caccgtctcc					360
tca					363

<210> SEQ ID NO 226
<211> LENGTH: 121
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Asn Trp Ala Arg Gln Ala Pro Gly Lys Gly Leu Glu Trp Val
        35                  40                  45

Ser Gly Ile Thr Gly Ser Gly Ala Thr Tyr Tyr Ala Asp Ser Val
    50                  55                  60

Lys Gly Arg Phe Thr Ile Ser Arg Glu Asn Ser Lys Asn Thr Leu Phe
65                  70                  75                  80

Leu Gln Met Asp Thr Leu Arg Ala Glu Asp Thr Ala Val Tyr Tyr Cys
                85                  90                  95

Ala Lys Asp Arg Arg Tyr Phe Pro Thr Ser Gly Gly Pro Gln Trp Gly
            100                 105                 110

Gln Gly Thr Leu Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 227
ggattcacct tcagaaacta tgcc                                          24

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 228

Gly Phe Thr Phe Arg Asn Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 229
attactggta gtggtggtgc caca                                          24

<210> SEQ ID NO 230
<211> LENGTH: 8
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 230

Ile Thr Gly Ser Gly Gly Ala Thr
1               5

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcgaaagatc ggaggtattt ccctacttcg gggggtcctc ag                        42

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ala Lys Asp Arg Arg Tyr Phe Pro Thr Ser Gly Gly Pro Gln
1               5                   10

<210> SEQ ID NO 233
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gatattgtga tgactcagtc tccactctcc ctgcccgtca cccctggaga gccggcctcc     60
atctcctgca ggtcttctcg gagcctcctg catagttctg gatacaacta tttggattgg    120
tacctgcaga agccagggca gtctccacag ctcctgctct atttgggttc taatcgggcc    180
tccggggtcc ctgacaggtt cagtggcagt ggatcaggca catatttac actgaaaatc     240 agcagagtgg acgctgaaga tgttgggggtt tattactgca tgcaagctct acaaactccg    300
tggacgttcg gccaagggac caaggtggaa atcaaa                              336

<210> SEQ ID NO 234
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Asp Ile Val Met Thr Gln Ser Pro Leu Ser Leu Pro Val Thr Pro Gly
1               5                   10                  15

Glu Pro Ala Ser Ile Ser Cys Arg Ser Ser Arg Ser Leu Leu His Ser
            20                  25                  30

Ser Gly Tyr Asn Tyr Leu Asp Trp Tyr Leu Gln Lys Pro Gly Gln Ser
        35                  40                  45

```
Pro Gln Leu Leu Leu Tyr Leu Gly Ser Asn Arg Ala Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Asp Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 235
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
cggagcctcc tgcatagttc tggatacaac tat                             33

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Arg Ser Leu Leu His Ser Ser Gly Tyr Asn Tyr
1               5                   10
```

<210> SEQ ID NO 237
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237 ttgggttct                                                         9

<210> SEQ ID NO 238
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Leu Gly Ser
1
```

<210> SEQ ID NO 239
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
atgcaagctc tacaaactcc gtggacg                                    27

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 240

Met Gln Ala Leu Gln Thr Pro Trp Thr
1               5

<210> SEQ ID NO 241
<211> LENGTH: 348
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 241
gaggtgcagc tggtggagtc tgggggaggc ttggtccagc cggggggtc cctgagactc      60 tcctgtgcag cctctggatt cacctttagt agctttagga tgacctgggt ccgccaggct    120
ccagggaagg ggctggagtg ggtggccaac ataaagcaag atggaagtga aaatactat     180 gtggactctg tgaagggccg attcaccatc tccagagaca acgccaagaa ctcactgtat    240
ctgcaaatga acagcctgag agccgaggac acggctgtgt attactgtgc gagagggggg    300
ggtatagcag cttactgggg ccagggaacc ctggtcaccg tctcctca                 348

<210> SEQ ID NO 242
<211> LENGTH: 116
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 242

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Arg Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ile Ala Ala Tyr Trp Gly Gln Gly Thr Leu Val
            100                 105                 110

Thr Val Ser Ser
        115

<210> SEQ ID NO 243
<211> LENGTH: 24
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 243
ggattcacct ttagtagctt tagg                                          24

<210> SEQ ID NO 244
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gly Phe Thr Phe Ser Ser Phe Arg
1               5

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
ataaagcaag atggaagtga gaaa                                          24

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ile Lys Gln Asp Gly Ser Glu Lys
1               5

<210> SEQ ID NO 247
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gcgagagggg ggggtatagc agcttac                                       27

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Arg Gly Gly Gly Ile Ala Ala Tyr
1               5

<210> SEQ ID NO 249
<211> LENGTH: 324
<212> TYPE: DNA

-continued

<213> ORGANISM: Artificial Sequence
<220> FEATURE:
<223> OTHER INFORMATION: Description of Artificial Sequence: Synthetic
      polynucleotide

<400> SEQUENCE: 249
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                          324

<210> SEQ ID NO 250
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
cagagcatta gcagctat                                                  18

<210> SEQ ID NO 252
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Ser Ile Ser Ser Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 253 gctgcatcc                                                                                         9

<210> SEQ ID NO 254
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Ala Ala Ser
1

<210> SEQ ID NO 255
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 255
caacagagtt acagtacccc tccgatcacc                                                                 30

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Gln Gln Ser Tyr Ser Thr Pro Pro Ile Thr
1               5                   10

<210> SEQ ID NO 257
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 257
gaggtgcagc tggtggagtc tgggggaggc ttggtacagc ctgggggtc cctgagactc        60 tcctgtgcag cctctggatt cacctttagc agctatgcca tgagctgggt ccgccaggct       120
ccagggaagg gctggagtg gtctcagct attagtggta gtggtggtag cacatactac        180
gcagactccg tgaagggccg gttcaccatc tccagagaca attccaagaa cacgctgtat       240
ctgcaaatga acagcctgag agccgaggac acggccgtat attactgtgc gaaagatcgg       300
ggggaaaacc ggtattacta ctactactac ggtatggacg tctggggcca agggaccacg       360
gtcaccgtct cctca                                                        375

```
<210> SEQ ID NO 258
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Glu Asn Arg Tyr Tyr Tyr Tyr Tyr Gly Met
            100                 105                 110

Asp Val Trp Gly Gln Gly Thr Thr Val Thr Val Ser Ser
        115                 120                 125

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggattcacct ttagcagcta tgcc                                              24

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Phe Thr Phe Ser Ser Tyr Ala
1               5

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
attagtggta gtggtggtag caca                                              24

<210> SEQ ID NO 262
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 262

Ile Ser Gly Ser Gly Gly Ser Thr
1               5

<210> SEQ ID NO 263
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gcgaaagatc gggggaaaa ccggtattac tactactact acggtatgga cgtc            54

<210> SEQ ID NO 264
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ala Lys Asp Arg Gly Glu Asn Arg Tyr Tyr Tyr Tyr Tyr Gly Met
1               5                   10                  15

Asp Val

<210> SEQ ID NO 265
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265
caggtgcagc tggtggagtc tgggggaggc gtggtccagc ctggagggtc cctgagactc     60
tcctgtacag cctctggatt caccttcaat aactatggca tccactgggt ccgccaggct    120
ccaggcaagg ggctggaatg ggtggcagtt atatcatatg atggaagtaa taaattctat    180
gcagagtccg tgaggggccg attcaccatc tccagagaca attccaggaa cacactgttt    240
ctgcagatga tcagcctgcg aggtgaggac tcggctgttt attactgtgc gaaagatcga    300
ccctattacg atattttgac tgctcattat ccctctgact actacttcta cgctatggac    360
gtctggggcc atgggaccac ggtcaccgtc tcctca                              396

<210> SEQ ID NO 266
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Asn Asn Tyr
            20                  25                  30
```

Gly Ile His Trp Val Arg Gln Ala Pro Gly Lys Gly Leu Glu Trp Val
            35                  40                  45

Ala Val Ile Ser Tyr Asp Gly Ser Asn Lys Phe Tyr Ala Glu Ser Val
        50                  55                  60

Arg Gly Arg Phe Thr Ile Ser Arg Asp Asn Ser Arg Asn Thr Leu Phe
65                  70                  75                  80

Leu Gln Met Ile Ser Leu Arg Gly Glu Asp Ser Ala Val Tyr Tyr Cys
                85                  90                  95

Ala Lys Asp Arg Pro Tyr Tyr Asp Ile Leu Thr Ala His Tyr Pro Ser
            100                 105                 110

Asp Tyr Tyr Phe Tyr Ala Met Asp Val Trp Gly His Gly Thr Thr Val
            115                 120                 125

Thr Val Ser Ser
    130

<210> SEQ ID NO 267
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ggattcacct tcaataacta tggc                                              24

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Phe Thr Phe Asn Asn Tyr Gly
1               5

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
atatcatatg atggaagtaa taaa                                              24

<210> SEQ ID NO 270
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ile Ser Tyr Asp Gly Ser Asn Lys
1               5

<210> SEQ ID NO 271
<211> LENGTH: 75

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gcgaaagatc gaccctatta cgatattttg actgctcatt atccctctga ctactacttc    60
tacgctatgg acgtc                                                    75

<210> SEQ ID NO 272
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Lys Asp Arg Pro Tyr Tyr Asp Ile Leu Thr Ala His Tyr Pro Ser
1               5                   10                  15

Asp Tyr Tyr Phe Tyr Ala Met Asp Val
            20                  25

<210> SEQ ID NO 273
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 273
caggtgcagc tggtggagtc tgggggaggc gtggtccagc ctgggaggtc cctgagactc    60
tcctgtgcag cctctggctt caccttcact aactatgcca tgcactgggt ccgccaggct   120
ccaggcaagg gactggagtg gtggcagtt atatcatatg atggaagtca cacatacttt    180
gcagactccg tgaagggccg attcaccatg tccagagaca attccaagaa cacgatatct   240
ctacaaatga acagtctgag acctgaggac acggctgttt attttgtgc gggaggagga    300 gctactacgt ggttctactt ttacggtttg acgtctggg gccaagggac cacggtcacc    360
gtctcctca                                                          369

<210> SEQ ID NO 274
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser His Thr Tyr Phe Ala Asp Ser Val
    50                  55                  60

Lys Gly Arg Phe Thr Met Ser Arg Asp Asn Ser Lys Asn Thr Ile Ser
65                  70                  75                  80

Leu Gln Met Asn Ser Leu Arg Pro Glu Asp Thr Ala Val Tyr Phe Cys
            85                  90                  95

Ala Gly Gly Gly Ala Thr Thr Trp Phe Tyr Phe Gly Leu Asp Val
        100                 105                 110

Trp Gly Gln Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
ggcttcacct tcactaacta tgcc                                          24

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Gly Phe Thr Phe Thr Asn Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
atatcatatg atggaagtca caca                                          24

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ile Ser Tyr Asp Gly Ser His Thr
1               5

<210> SEQ ID NO 279
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gcgggaggag gagctactac gtggttctac ttttacggtt tggacgtc                48

<210> SEQ ID NO 280

<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Gly Gly Gly Ala Thr Thr Trp Phe Tyr Phe Tyr Gly Leu Asp Val
1               5                   10                  15

<210> SEQ ID NO 281
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 281
gaggtgcagc tggtggagtc tgggggaggc ttggtaaaac cggggggggtc ccttagactc      60 tcctgtacag cctctggatt cactttcggt aatgcctgga tgagctgggt ccggcaggct     120
ccagggaagg gcctggagtg ggttggcctt attaaaggta aaactgatgg tgggacaaca     180
aactacgctg cacccgtgaa aggcagattc accatctcaa gagatgattc aaaaaacacg     240
ctgtatctgc atttgaacag cctgagaacc gaggacacag ccttgtatta ctgtaccaca     300
gatcaggtgg aactacgaca atactactac tacggtttgg acgtctgggg ccaggggacc     360
acggtcaccg tctcctca                                                   378

<210> SEQ ID NO 282
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Glu Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Gly Asn Ala
            20                  25                  30

Trp Met Ser Trp Val Arg Gln Ala Pro Gly Lys Gly Leu Glu Trp Val
        35                  40                  45

Gly Leu Ile Lys Gly Lys Thr Asp Gly Gly Thr Thr Asn Tyr Ala Ala
    50                  55                  60

Pro Val Lys Gly Arg Phe Thr Ile Ser Arg Asp Asp Ser Lys Asn Thr
65                  70                  75                  80

Leu Tyr Leu His Leu Asn Ser Leu Arg Thr Glu Asp Thr Ala Leu Tyr
                85                  90                  95

Tyr Cys Thr Thr Asp Gln Val Glu Leu Arg Gln Tyr Tyr Tyr Tyr Gly
            100                 105                 110

Leu Asp Val Trp Gly Gln Gly Thr Thr Val Thr Val Ser Ser
        115                 120                 125

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 283
ggattcactt tcggtaatgc ctgg                                            24

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Phe Thr Phe Gly Asn Ala Trp
1               5

<210> SEQ ID NO 285
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
attaaaggta aaactgatgg tgggacaaca                                      30

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ile Lys Gly Lys Thr Asp Gly Gly Thr Thr
1               5                   10

<210> SEQ ID NO 287
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
accacagatc aggtggaact acgacaatac tactactacg gtttggacgt c              51

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Thr Thr Asp Gln Val Glu Leu Arg Gln Tyr Tyr Tyr Tyr Gly Leu Asp
1               5                   10                  15

Val

<210> SEQ ID NO 289
<211> LENGTH: 354

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
gaggtgcagc tggtggagtc tgggggaggc ttggtacagc cagggcggtc cctgagactc    60
tcctgtacag cttctggatt cagctttggt gataatgcta tgggctgggt ccgccaggct   120
ccagggaagg ggctggagtg ggtaagtttc attagaagga aagcttctgg tgggacaaca   180
gaatacgccg cgtctgtgaa aggcagattc accatctcaa gagatgattc caaaagcatc   240
gcctatctgc aaatgaacag tctgaaaacc gaggacacag gcgtttatta ttgtactaga   300
ggaggagcag tgtacggcta ctggggccag ggaaccctgg tcaccgtctc ctca         354

<210> SEQ ID NO 290
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Phe Gly Asp Asn
            20                  25                  30

Ala Met Gly Trp Val Arg Gln Ala Pro Gly Lys Gly Leu Glu Trp Val
        35                  40                  45

Ser Phe Ile Arg Arg Lys Ala Ser Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Gly Val Tyr
                85                  90                  95

Tyr Cys Thr Arg Gly Gly Ala Val Tyr Gly Tyr Trp Gly Gln Gly Thr
            100                 105                 110

Leu Val Thr Val Ser Ser
        115

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ggattcagct ttggtgataa tgct                                           24

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292
```

```
Gly Phe Ser Phe Gly Asp Asn Ala
1               5
```

<210> SEQ ID NO 293
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
attagaagga aagcttctgg tgggacaaca                                      30

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

```
Ile Arg Arg Lys Ala Ser Gly Gly Thr Thr
1               5                   10
```

<210> SEQ ID NO 295
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
actagaggag gagcagtgta cggctac                                         27

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

```
Thr Arg Gly Gly Ala Val Tyr Gly Tyr
1               5
```

<210> SEQ ID NO 297
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcaagg ggctggagtg gtggcagtt atatggtatg atggaagtaa taatactat      180 gcagactccg tgaagggccg attcaccatc tccagagaca attccaagaa cacgctgtat     240
ctgcaaatga acagcctgag agccgaggac acggctgttt attactgtgc gagagattgg     300
gtacgatttt tggagtggtt tccccacttt gactactggg gccagggaac cctggtcacc     360

```

-continued gtctcctca                                                        369

<210> SEQ ID NO 298
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Val Arg Phe Leu Glu Trp Phe Pro His Phe Asp Tyr
            100                 105                 110

Trp Gly Gln Gly Thr Leu Val Thr Val Ser Ser
        115                 120

<210> SEQ ID NO 299
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ggattcacct tcagtagcta tggc                                       24

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Phe Thr Phe Ser Ser Tyr Gly
1               5

<210> SEQ ID NO 301
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
atatggtatg atggaagtaa taaa                                       24

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Ile Trp Tyr Asp Gly Ser Asn Lys
1               5

<210> SEQ ID NO 303
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
gcgagagatt gggtacgatt tttggagtgg tttccccact ttgactac         48

<210> SEQ ID NO 304
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Ala Arg Asp Trp Val Arg Phe Leu Glu Trp Phe Pro His Phe Asp Tyr
1               5                   10                  15

<210> SEQ ID NO 305
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 305
gaggtgcagc tggtggagtc tgggggaggc ttggtacagc ctggggggtc cctgagactc    60
tcctgtgcag cctctggatt caccttagc aactatgcca tgagctgggt ccgccaggtt   120
ccagggaagg ggctggagtg ggtctcaact attagtggta gtggtggtag cacatactac   180
gcagactccg tgaagggccg gttcaccatc tccagagaca attccaagaa ctcgctgtat   240
ctgcaaatga acagcctgag agccgaggac acggccgtat attattgtgc gaaattggtt   300
cggggagtta ttggctggtt cgaccctgg ggccagggaa ccctggtcac cgtctcctca   360

<210> SEQ ID NO 306
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 306

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Val Pro Gly Lys Gly Leu Glu Trp Val
            35                  40                  45

Ser Thr Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Leu Val Arg Gly Val Ile Gly Trp Phe Asp Pro Trp Gly Gln
            100                 105                 110

Gly Thr Leu Val Thr Val Ser Ser
            115                 120

<210> SEQ ID NO 307
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggattcacct ttagcaacta tgcc                                           24

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Phe Thr Phe Ser Asn Tyr Ala
1               5

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
attagtggta gtggtggtag caca                                           24

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ile Ser Gly Ser Gly Gly Ser Thr
1               5

<210> SEQ ID NO 311
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 311
gcgaaattgg ttcggggagt tattggctgg ttcgacccc                                 39

<210> SEQ ID NO 312
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ala Lys Leu Val Arg Gly Val Ile Gly Trp Phe Asp Pro
1               5                   10

<210> SEQ ID NO 313
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 313
caggtgcagc tggtggagtc tgggggaggc gtggtccagc ctggaggtc cgtgagactc           60 tcctgtggag cgtctggatt cactttcaaa tactatggca tgcactgggt ccgccaggct         120
ccaggcaagg ggctggaatg ggtggcagtc atttggtatg atggaagaaa taaattttat         180
gcagactctg tgaagggccg cttcactatc tccagagaca attccaagaa cacggtgaat         240
ctggaaatga acaacctgag agccgaggac acggctatat attactgtgc gagagatgga         300
ggaacagcgg atggcgacta ttttgactac tggggccagg gaaccctggt caccgtctcc         360
tca                                                                      363

<210> SEQ ID NO 314
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Gln Val Gln Leu Val Glu Ser Gly Gly Gly Val Val Gln Pro Gly Arg
1               5                   10                  15

Ser Val Arg Leu Ser Cys Gly Ala Ser Gly Phe Thr Phe Lys Tyr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Phe Tyr Ala Asp Ser Val
    50                  55                  60

Lys Gly Arg Phe Thr Ile Ser Arg Asp Asn Ser Lys Asn Thr Val Asn
65                  70                  75                  80

Leu Glu Met Asn Asn Leu Arg Ala Glu Asp Thr Ala Ile Tyr Tyr Cys
                85                  90                  95

Ala Arg Asp Gly Gly Thr Ala Asp Gly Asp Tyr Phe Asp Tyr Trp Gly
            100                 105                 110

Gln Gly Thr Leu Val Thr Val Ser Ser

```
                                115              120
```

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
ggattcactt tcaaatacta tggc                                              24

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gly Phe Thr Phe Lys Tyr Tyr Gly
1               5

<210> SEQ ID NO 317
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
atttggtatg atggaagaaa taaa                                              24

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Ile Trp Tyr Asp Gly Arg Asn Lys
1               5

<210> SEQ ID NO 319
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gcgagagatg gaggaacagc ggatggcgac tattttgact ac                          42

<210> SEQ ID NO 320
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ala Arg Asp Gly Gly Thr Ala Asp Gly Asp Tyr Phe Asp Tyr
1               5                   10

<210> SEQ ID NO 321
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 321
gaaatagttt tgacacagag tcccggcaca ctgtcactct ctcccgggga aagagccacc    60
ttgtcatgta gagcaagtca gtcagtctct agctcttatc tcgcctggta ccagcagaag   120
ccgggacagg ccctagact gctgatctac ggggcaagtt ccagggccac cggaatcccc   180
gaccggttca gtggaagcgg aagcggaacc gattttactt tgacgatttc tagactggag   240
ccagaggatt tcgccgttta ctattgtcaa cagtacggaa gcagcccgtg acgtttggc   300 cagggcacga aggtagaaat caag                                          324

<210> SEQ ID NO 322
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 323
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
agagcaagtc agtcagtctc tagctcttat ctcgcc                              36

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Arg Ala Ser Gln Ser Val Ser Ser Ser Tyr Leu Ala
1               5                   10

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
ggggcaagtt ccagggccac c                                             21

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Ala Ser Ser Arg Ala Thr
1               5

<210> SEQ ID NO 327
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
caacagtacg gaagcagccc gtggacg                                       27

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Gln Tyr Gly Ser Ser Pro Trp Thr
1               5

<210> SEQ ID NO 329
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 329
gaggtgcagc tggtggagtc tgggggaggt tggtacagc ctggggggtc cctgagactc      60
tcctgtgtag gcactggatt cacctttagc aactatgcca tgagctgggt ccgccaggct    120
ccagggaagg ggctggagtg ggtctcaggt attagtggta gaagtagtgg cacattctac    180
gcagactccg tgaagggccg gttcaccatc tccagagaca attcccagaa tacgctgtat    240

```
ctgcaaatga acagcctggg agccgaggac acggccgtat attactgtgc gaaagtttcc    300
cgttataact gggactacgt cccctttgac ttctggggcc agggaaccct ggtcaccgtc    360
tcctca                                                                366
```

<210> SEQ ID NO 330
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

```
Glu Val Gln Leu Val Glu Ser Gly Gly Gly Leu Val Gln Pro Gly Gly
1               5                   10                  15

Ser Leu Arg Leu Ser Cys Val Gly Thr Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Gly Arg Ser Ser Gly Thr Phe Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Gly Ala Glu Asp Thr Ala Val Tyr Tyr Cys
                85                  90                  95

Ala Lys Val Ser Arg Tyr Asn Trp Asp Tyr Val Pro Phe Asp Phe Trp
            100                 105                 110

Gly Gln Gly Thr Leu Val Thr Val Ser Ser
        115                 120
```

<210> SEQ ID NO 331
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331

```
ggattcacct ttagcaacta tgcc                                            24
```

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

```
Gly Phe Thr Phe Ser Asn Tyr Ala
1               5
```

<210> SEQ ID NO 333
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333

-continued

```
attagtggta gaagtagtgg caca                                              24

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ile Ser Gly Arg Ser Ser Gly Thr
1               5

<210> SEQ ID NO 335
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gcgaaagttt cccgttataa ctgggactac gtcccctttg acttc                       45

<210> SEQ ID NO 336
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Lys Val Ser Arg Tyr Asn Trp Asp Tyr Val Pro Phe Asp Phe
1               5                   10                  15

<210> SEQ ID NO 337
<211> LENGTH: 39
<212> TYPE: PRT
<213> ORGANISM: Homo sapiens
<220> FEATURE:
<223> OTHER INFORMATION: Human AngPTL8 Naked Peptide: amino acids 22-60
<300> PUBLICATION INFORMATION:
<308> DATABASE ACCESSION NUMBER: GenBank Database: NP_061157.3

<400> SEQUENCE: 337

Ala Pro Met Gly Gly Pro Glu Leu Ala Gln His Glu Glu Leu Thr Leu
1               5                   10                  15

Leu Phe His Gly Thr Leu Gln Leu Gly Gln Ala Leu Asn Gly Val Tyr
            20                  25                  30

Arg Thr Thr Glu Gly Arg Leu
        35

<210> SEQ ID NO 338
<211> LENGTH: 26
<212> TYPE: PRT
<213> ORGANISM: Homo sapiens
<220> FEATURE:
<223> OTHER INFORMATION: Human ANGPTL3 Shift Naked Peptide: amino acids
      32-57
<300> PUBLICATION INFORMATION:
<308> DATABASE ACCESSION NUMBER: GenBank Database: NP_055310.1

<400> SEQUENCE: 338

Glu Pro Lys Ser Arg Phe Ala Met Leu Asp Asp Val Lys Ile Leu Ala
1               5                   10                  15
```

```
                1               5              10              15
Asn Gly Leu Leu Gln Leu Gly His Gly Leu
                20                      25
```

<210> SEQ ID NO 339
<211> LENGTH: 34
<212> TYPE: PRT
<213> ORGANISM: Homo sapiens
<220> FEATURE:
<223> OTHER INFORMATION: Human ANGPTL4 Naked Peptide: amino acids 34-67
<300> PUBLICATION INFORMATION:
<308> DATABASE ACCESSION NUMBER: GenBank Database: NP_001034756.1

<400> SEQUENCE: 339

```
Arg Phe Ala Ser Trp Asp Glu Met Asn Val Leu Ala His Gly Leu Leu
1               5                      10                      15

Gln Leu Gly Gln Gly Leu Arg Glu His Ala Glu Arg Thr Arg Ser Gln
                20                      25                      30

Leu Cys
```

<210> SEQ ID NO 340
<211> LENGTH: 413
<212> TYPE: PRT
<213> ORGANISM: Artificial Sequence
<220> FEATURE:
<223> OTHER INFORMATION: Description of Artificial Sequence: Synthetic
      hANGPTL8-mFc aa 1-177: amino acids 22-198 of NP_061157.3 aa
      178-413: GPG linker and mouse IgG2a Fc tag polypeptide
<300> PUBLICATION INFORMATION:
<308> DATABASE ACCESSION NUMBER: GenBank Database: NP_061157.3 (part of
      full length sequence)

<400> SEQUENCE: 340

```
Ala Pro Met Gly Gly Pro Glu Leu Ala Gln His Glu Glu Leu Thr Leu
1               5                      10                      15

Leu Phe His Gly Thr Leu Gln Leu Gly Gln Ala Leu Asn Gly Val Tyr
                20                      25                      30

Arg Thr Thr Glu Gly Arg Leu Thr Lys Ala Arg Asn Ser Leu Gly Leu
                35                      40                      45

Tyr Gly Arg Thr Ile Glu Leu Leu Gly Gln Glu Val Ser Arg Gly Arg
50                      55                      60

Asp Ala Ala Gln Glu Leu Arg Ala Ser Leu Leu Glu Thr Gln Met Glu
65                      70                      75                      80

Glu Asp Ile Leu Gln Leu Gln Ala Glu Ala Thr Ala Glu Val Leu Gly
                85                      90                      95

Glu Val Ala Gln Ala Gln Lys Val Leu Arg Asp Ser Val Gln Arg Leu
                100                     105                     110

Glu Val Gln Leu Arg Ser Ala Trp Leu Gly Pro Ala Tyr Arg Glu Phe
        115                     120                     125

Glu Val Leu Lys Ala His Ala Asp Lys Gln Ser His Ile Leu Trp Ala
        130                     135                     140

Leu Thr Gly His Val Gln Arg Gln Arg Arg Glu Met Val Ala Gln Gln
145                     150                     155                     160

His Arg Leu Arg Gln Ile Gln Glu Arg Leu His Thr Ala Ala Leu Pro
                165                     170                     175

Ala Gly Pro Gly Glu Pro Arg Gly Pro Thr Ile Lys Pro Cys Pro Pro
                180                     185                     190

Cys Lys Cys Pro Ala Pro Asn Leu Leu Gly Gly Pro Ser Val Phe Ile
        195                     200                     205
```

```
Phe Pro Pro Lys Ile Lys Asp Val Leu Met Ile Ser Leu Ser Pro Ile
    210                 215                 220

Val Thr Cys Val Val Asp Val Ser Glu Asp Pro Asp Val Gln
225             230                 235                 240

Ile Ser Trp Phe Val Asn Asn Val Glu Val His Thr Ala Gln Thr Gln
                245                 250                 255

Thr His Arg Glu Asp Tyr Asn Ser Thr Leu Arg Val Val Ser Ala Leu
            260                 265                 270

Pro Ile Gln His Gln Asp Trp Met Ser Gly Lys Glu Phe Lys Cys Lys
        275                 280                 285

Val Asn Asn Lys Asp Leu Pro Ala Pro Ile Glu Arg Thr Ile Ser Lys
290                 295                 300

Pro Lys Gly Ser Val Arg Ala Pro Gln Val Tyr Val Leu Pro Pro Pro
305                 310                 315                 320

Glu Glu Glu Met Thr Lys Lys Gln Val Thr Leu Thr Cys Met Val Thr
                325                 330                 335

Asp Phe Met Pro Glu Asp Ile Tyr Val Glu Trp Thr Asn Asn Gly Lys
            340                 345                 350

Thr Glu Leu Asn Tyr Lys Asn Thr Glu Pro Val Leu Asp Ser Asp Gly
        355                 360                 365

Ser Tyr Phe Met Tyr Ser Lys Leu Arg Val Glu Lys Lys Asn Trp Val
370                 375                 380

Glu Arg Asn Ser Tyr Ser Cys Ser Val Val His Glu Gly Leu His Asn
385                 390                 395                 400

His His Thr Thr Lys Ser Phe Ser Arg Thr Pro Gly Lys
                405                 410

<210> SEQ ID NO 341
<211> LENGTH: 410
<212> TYPE: PRT
<213> ORGANISM: Artificial Sequence
<220> FEATURE:
<223> OTHER INFORMATION: Description of Artificial Sequence: Synthetic
      MfAngPTL8-mFc aa 1-177: amino acids 78-254 of XP_005588064.1aa
      178-410: mouse IgG2a Fc tag polypeptide
<300> PUBLICATION INFORMATION:
<308> DATABASE ACCESSION NUMBER: GenBank Database: XP_005588064.1 (part
      of full length sequence)

<400> SEQUENCE: 341

Ala Pro Val Gly Ser Pro Glu Leu Ala Glu His Glu Leu Thr Leu
1               5                   10                  15

Leu Phe His Gly Thr Leu Gln Leu Gly Gln Ala Leu Asn Gly Val Tyr
            20                  25                  30

Lys Thr Thr Glu Gly Arg Leu Thr Lys Ala Arg Asn Ser Leu Gly Leu
        35                  40                  45

Tyr Gly Arg Thr Val Glu Leu Leu Gly Gln Glu Val Ser Arg Gly Arg
50                  55                  60

Asp Ala Ala Gln Glu Leu Arg Ala Ser Leu Leu Glu Thr Gln Met Glu
65                  70                  75                  80

Glu Asp Ile Leu Gln Leu Lys Ala Glu Ala Ile Ala Glu Val Leu Glu
                85                  90                  95

Glu Val Ala Gln Ala Gln Lys Val Leu Gln Asp Ser Val Arg Arg Leu
            100                 105                 110

Glu Val Gln Leu Arg Ser Ala Trp Leu Gly Pro Ala Tyr Gln Glu Phe
        115                 120                 125

Glu Val Leu Lys Ala His Ala Asp Lys Gln Ser His Ile Leu Trp Ala
```

```
                130             135              140
Leu Thr Gly His Val Gln Arg Gln Arg Glu Met Val Ala Gln Gln
145                 150                 155                 160

His Arg Leu Arg Gln Ile Gln Glu Arg Ile His Lys Ala Ala Leu Pro
            165                 170                 175

Ala Glu Pro Arg Gly Pro Thr Ile Lys Pro Cys Pro Pro Cys Lys Cys
            180                 185                 190

Pro Ala Pro Asn Leu Leu Gly Gly Pro Ser Val Phe Ile Phe Pro Pro
            195                 200                 205

Lys Ile Lys Asp Val Leu Met Ile Ser Leu Ser Pro Ile Val Thr Cys
            210                 215                 220

Val Val Val Asp Val Ser Glu Asp Asp Pro Asp Val Gln Ile Ser Trp
225                 230                 235                 240

Phe Val Asn Asn Val Glu Val His Thr Ala Gln Thr Gln Thr His Arg
                245                 250                 255

Glu Asp Tyr Asn Ser Thr Leu Arg Val Val Ser Ala Leu Pro Ile Gln
                260                 265                 270

His Gln Asp Trp Met Ser Gly Lys Glu Phe Lys Cys Lys Val Asn Asn
            275                 280                 285

Lys Asp Leu Pro Ala Pro Ile Glu Arg Thr Ile Ser Lys Pro Lys Gly
290                 295                 300

Ser Val Arg Ala Pro Gln Val Tyr Val Leu Pro Pro Pro Glu Glu Glu
305                 310                 315                 320

Met Thr Lys Lys Gln Val Thr Leu Thr Cys Met Val Thr Asp Phe Met
                325                 330                 335

Pro Glu Asp Ile Tyr Val Glu Trp Thr Asn Asn Gly Lys Thr Glu Leu
                340                 345                 350

Asn Tyr Lys Asn Thr Glu Pro Val Leu Asp Ser Asp Gly Ser Tyr Phe
            355                 360                 365

Met Tyr Ser Lys Leu Arg Val Glu Lys Lys Asn Trp Val Glu Arg Asn
370                 375                 380

Ser Tyr Ser Cys Ser Val Val His Glu Gly Leu His Asn His His Thr
385                 390                 395                 400

Thr Lys Ser Phe Ser Arg Thr Pro Gly Lys
                405                 410

<210> SEQ ID NO 342
<211> LENGTH: 460
<212> TYPE: PRT
<213> ORGANISM: Artificial Sequence
<220> FEATURE:
<223> OTHER INFORMATION: Description of Artificial Sequence: Synthetic
      hANGPTL3 polypeptide

<400> SEQUENCE: 342

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80
```

```
Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
            115                 120                 125

Glu Glu Lys Ile Leu Leu Gln Gln Lys Val Lys Tyr Leu Glu Glu Gln
        130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 343
<211> LENGTH: 1383
<212> TYPE: DNA
<213> ORGANISM: Artificial Sequence
<220> FEATURE:
<223> OTHER INFORMATION: Description of Artificial Sequence: Synthetic
``` hANGPTL3 polynucleotide

<400> SEQUENCE: 343

```
atgttcacaa ttaagctcct tcttttatt gttcctctag ttatttcctc cagaattgat     60
caagacaatt catcatttga ttctctatct ccagagccaa atcaagatt tgctatgtta    120
gacgatgtaa aaattttagc caatggcctc cttcagttgg acatggtct taaagacttt    180
gtccataaga cgaagggcca aattaatgac atatttcaaa aactcaacat atttgatcag    240
tcttttatg atctatcgct gcaaaccagt gaaatcaaag aagaagaaaa ggaactgaga    300
agaactacat ataaactaca agtcaaaaat gaagaggtaa agaatatgtc acttgaactc    360
aactcaaaac ttgaaagcct cctagaagaa aaaattctac ttcaacaaaa agtgaaatat    420
ttagaagagc aactaactaa cttaattcaa aatcaacctg aaactccaga cacccagaa    480
gtaacttcac ttaaaacttt tgtagaaaaa caagataata gcatcaaaga ccttctccag    540
accgtggaag accaatataa acaattaaac caacagcata gtcaaataaa agaaatagaa    600
atcagctca gaaggactag tattcaagaa cccacagaaa tttctctatc ttccaagcca    660
agagcaccaa gaactactcc ctttcttcag ttgaatgaaa taagaaatgt aaaacatgat    720
ggcattcctg ctgaatgtac caccatttat aacagaggtg aacatacaag tggcatgtat    780
gccatcagac ccagcaactc tcaagttttt catgtctact gtgatgttat atcaggtagt    840
ccatggacat taattcaaca tcgaatagat ggatcacaaa acttcaatga acgtgggag    900
aactacaaat atggttttgg gaggcttgat ggagaatttt ggttgggcct agagaagata    960
tactccatag tgaagcaatc taattatgtt ttacgaattg agttggaaga ctggaaagac   1020
aacaaacatt atattgaata ttcttttttac ttgggaaatc acgaaaccaa ctatacgcta   1080
catctagttg cgattactgg caatgtcccc aatgcaatcc cggaaaacaa agattggtg   1140
ttttctactt gggatcacaa agcaaaagga cacttcaact gtccagaggg ttattcagga   1200
ggctggtggt ggcatgatga gtgtggagaa acaacctaa atggtaaata taacaaacca   1260
agagcaaaat ctaagccaga gaggagaaga ggattatctt ggaagtctca aaatggaagg   1320
ttatactcta taaatcaac caaaatgttg atccatccaa cagattcaga aagctttgaa   1380
tga                                                                1383
```

<210> SEQ ID NO 344
<211> LENGTH: 406
<212> TYPE: PRT
<213> ORGANISM: Artificial Sequence
<220> FEATURE:
<223> OTHER INFORMATION: Description of Artificial Sequence: Synthetic hANGPTL4 polypeptide

<400> SEQUENCE: 344

```
Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
```

```
                85                  90                  95
Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
            115                 120                 125

His Leu Glu Lys Gln His Leu Arg Ile Gln His Leu Gln Ser Gln Phe
        130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Lys Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 345
<211> LENGTH: 1221
<212> TYPE: DNA
<213> ORGANISM: Artificial Sequence
<220> FEATURE:
<223> OTHER INFORMATION: Description of Artificial Sequence: Synthetic
      hANGPTL4 polynucleotide

<400> SEQUENCE: 345
atgagcggtg ctccgacggc cggggcagcc ctgatgctct cgccgccac cgccgtgcta    60 ctgagcgctc agggcggacc cgtgcagtcc aagtcgccgc gctttgcgtc ctggacgag   120 atgaatgtcc tggcgcacgg actcctgcag ctcggccagg ggctgcgcga acacgcggag   180
```

```
cgcacccgca gtcagctgag cgcgctggag cggcgcctga gcgcgtgcgg gtccgcctgt      240
cagggaaccg aggggtccac cgacctcccg ttagcccctg agagccgggt ggaccctgag      300
gtccttcaca gcctgcagac acaactcaag gctcagaaca gcaggatcca gcaactcttc      360
cacaaggtgg cccagcagca gcggcacctg gagaagcagc acctgcgaat tcagcatctg      420
caaagccagt ttggcctcct ggaccacaag cacctagacc atgaggtggc caagcctgcc      480
cgaagaaaga ggctgcccga gatggccag ccagttgacc cggctcacaa tgtcagccgc       540
ctgcaccggc tgcccaggga ttgccaggag ctgttccagg ttggggagag gcagagtgga      600
ctatttgaaa tccagcctca ggggtctccg ccatttttgg tgaactgcaa gatgacctca      660
gatggaggct ggacagtaat tcagaggcgc cacgatggct cagtggactt caaccggccc      720
tgggaagcct acaaggcggg gtttggggat ccccacggcg agttctggct gggtctggag      780
aaggtgcata gcatcacggg ggaccgcaac agccgcctgg ccgtgcagct gcgggactgg      840
gatggcaacg ccgagttgct gcagttctcc gtgcacctgg gtggcgagga cacggcctat      900
agcctgcagc tcactgcacc cgtggccggc cagctgggcg ccaccaccgt cccacccagc      960
ggcctctccg tacccttctc cacttgggac caggatcacg acctccgcag ggacaagaac     1020
tgcgccaaga gcctctctgg aggctggtgg tttggcacct gcagccattc caacctcaac     1080
ggccagtact tccgctccat cccacagcag cggcagaagc ttaagaaggg aatcttctgg     1140
aagacctggc ggggccgcta ctacccgctg caggccacca ccatgttgat ccagcccatg     1200
gcagcagagg cagcctccta g                                              1221
```